US008952055B2

(12) United States Patent
Kaihatsu et al.

(10) Patent No.: US 8,952,055 B2
(45) Date of Patent: Feb. 10, 2015

(54) MEMBRANE FUSION INHIBITOR

(75) Inventors: Kunihiro Kaihatsu, Suita (JP); Shuichi Mori, Chiyoda-ku (JP); Tomo Daidoji, Suita (JP); Nobuo Kato, Suita (JP); Shinya Miyake, Suita (JP)

(73) Assignee: Protectea, Ltd., Osaka (JP)

( * ) Notice: Subject to any disclaimer, the term of this patent is extended or adjusted under 35 U.S.C. 154(b) by 523 days.

(21) Appl. No.: 12/865,360

(22) PCT Filed: Feb. 2, 2009

(86) PCT No.: PCT/JP2009/051721
§ 371 (c)(1),
(2), (4) Date: Sep. 24, 2010

(87) PCT Pub. No.: WO2009/096581
PCT Pub. Date: Aug. 6, 2009

(65) Prior Publication Data
US 2011/0003889 A1    Jan. 6, 2011

(30) Foreign Application Priority Data
Feb. 1, 2008    (JP) ................. 2008-023196

(51) Int. Cl.
| *A61K 31/35* | (2006.01) |
| *A61K 31/22* | (2006.01) |
| *A61K 31/353* | (2006.01) |
| *A61K 45/06* | (2006.01) |
| *C07D 311/62* | (2006.01) |

(52) U.S. Cl.
CPC ............... *A61K 31/353* (2013.01); *A61K 45/06* (2013.01); *C07D 311/62* (2013.01); *A61K 2300/00* (2013.01)
USPC ......................................... 514/456; 514/549

(58) Field of Classification Search
CPC .......................... A61K 31/353; A61K 2300/00
USPC .................................. 514/456, 549
See application file for complete search history.

(56) References Cited

U.S. PATENT DOCUMENTS

| 5,137,922 | A | 8/1992 | Shimamura et al. |
| 2006/0041010 | A1 | 2/2006 | Chan et al. |
| 2006/0134286 | A1 | 6/2006 | Maeda |
| 2006/0148726 | A1* | 7/2006 | Berg ............................ 514/27 |
| 2008/0058409 | A1 | 3/2008 | Fukami et al. |

FOREIGN PATENT DOCUMENTS

| CN | 1231277 | * 10/1999 |
| CN | 1650856 | 8/2005 |
| JP | 3-101623 | 4/1991 |
| JP | 2001-253879 | 9/2001 |
| JP | 2002-255810 | 9/2002 |
| JP | 2006-525796 | 11/2006 |
| JP | 2009-084266 | 4/2009 |
| WO | 03/094878 | 11/2003 |
| WO | 2004/076621 | 9/2004 |
| WO | 2006/021888 | 3/2006 |
| WO | 2006/080328 | 8/2006 |

(Continued)

OTHER PUBLICATIONS

CN 1231277. 1999 Machine translation.*
Chen et al. "Novel Long-chain-derivative of epigallocatachin-3-O-gallate prepared and purified from green tea polyphenols," Journal of Zhejiang University Science, 2003, vol. 4, No. 6, pp. 714-718.*
Toda et al., "Antibacterial and anti-hemolysin activities of tea catechins and their structural relatives", Japanese Journal of Bacteriology, 45 (2), 561-566, 1990—English Abstract on p. 566.
Hu et al., "Epigallocatechin Gallate Synergistically Enhances the Activity of Carbapenems against Methicillin-Resistant *Staphylococcus aureus*", Antimicrob. Agents Chemother., 46(2), 558-560, 2002.
Zhao et al., "Mechanism of Synergy between Epigallocatechin Gallate and β-Lactams against Methicillin-Resistant *Staphylococcus aureus*", Antimicrob. Agents Chemother., 45(6), 1737-1742, 2001.
Yanagawa et al., "A Combination Effect of Epigallocatechin Gallate, a Major Compound of Green Tea Catechins, with Antibiotics on *Helicobacter pylori* Growth In Vitro", Curr. Microbiol., 47, 244-249, 2003.

(Continued)

*Primary Examiner* — Shengjun Wang
(74) *Attorney, Agent, or Firm* — Hamre, Schumann, Mueller & Larson, P.C.

(57) ABSTRACT

The present invention provides a pharmaceutical composition that has excellent safety and targets a different step in the virus propagation cycle than conventional pharmaceutical compositions, applicable as an antiviral agent. A pharmaceutical composition containing an epigallocatechin gallate derivative represented by the following chemical formula (1), an isomer thereof, or a salt thereof is prepared. This can be used as a membrane fusion inhibitor that inhibits viral membrane fusion. In the following formula, $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of $R^1$ to $R^6$ is the acyl group. $R^7$ to $R^{16}$ are each a hydrogen atom, halogen, sodium, or potassium and may be identical to or different from one another.

12 Claims, 10 Drawing Sheets

(1)

(56) References Cited

FOREIGN PATENT DOCUMENTS

| WO | 2007/105280 | 9/2007 |
|---|---|---|
| WO | 2011/123942 | 10/2011 |

OTHER PUBLICATIONS

Hatano et al., "Enhancement of antibacterial effects of epigallocatechin gallate, using ascorbic acid", Phytochemistry, 69, 3111-3116, 2008.
Kida et al., "Identification of Biliary Metabolites of (—)-Epicallocatechin Gallate in Rats", J. Agric. Food Chem., 48, 4151-4155, 2000.
Mori et al., "Enhanced anti-influenza A virus activity of (—)-epigallocatechin-3-O-gallate fatty acid monoester derivatives: Effect of alkyl chain length", Bioorg. Med. Chem. Lett., 18, 4249-4252, 2008.
Utenova et al., "Antioxidant activity of O-protected derivatives of (—)-epigallocatechin-3-gallate: inhibition of soybean and rabbit 15-lipoxygenases", ARKIVOC, 9, 6-16, 2007.
Fudoji et al., "Research on Development of Lipophilic Catechin Derivatives (2)~ Development of Synthesis Method, and Radical Scavenging Activity and Antibacterial Activity~", Abstracts of Scientific Presentation in the 129th Annual Meeting of the Pharma—partial translation.
Zlydnikov, et al., "Study of rimantadine in the USSR: a review of the literature", Rev Infect Dis., 1981; 3(3): 408-421, Abstract only.
Duff, et al., "The transmembrane domain of influenza A M2 protein forms amantadine-sensitive proton channels in planar lipid bilayers", Virology 1992; 190(1): 485-489, Abstract only.
Woods, et al., "4-Guanidino-2,4-Dideoxy-2,3-Dehydro-*N*-Acetylneuraminic Acid is a Highly Effective Inhibitor both of the Sialidase (Neuraminidase) and of Growth of a Wide Range of Influenza A and B Viruses in Vitro", Antimicrobial Agents and Chemotherapy, 1993; 37(7): 1473-1479.
von Itzstein, et al., "Rational design of potent sialidase-based inhibitors of influenza virus replication", Nature 1993; 363(6428): 418-423, Abstract only.
Kim, et al., "Influenza neuraminidase inhibitors possessing a novel hydrophobic interaction in the enzyme active site: design, synthesis, and structural analysis of carbocyclic sialic acid analogues with potent anti-influenza activity", J Am Chem Soc 1997; 119(4): 681-690, Abstract only.
Lam, et al., A potential prodrug for a green tea plyphenol proteasome inhibitor: evaluation of the peracetate ester of (-)-epigallocatechin gallate [(-)-EGCG], Bioorganic & Medicinal Chemistry, 2004 12(21): 5587-5593.
Tanaka, et al., "Synthesis and Antioxidant Activity of Novel Amphipathic Derivatives of Tea Polyphenol", Bioorganic & Medicinal Chemistry Letters 1998; 8(14): 1801-1806.
Matsumura, et al., "Enhanced antitumor activities of (-)-epigallocatechin-3-O-gallate fatty acid monoester derivatives in vitro and in vivo", Biochemical and Biophysical Research Communications, vol. 377, No. 4, pp. 1118-1122, 2008.
Chen, et al., "Preparation, structure and antioxidant activity of EGCG palmitate", Journal of Zhejiang University (Science Edition), vol. 30, No. 4, pp. 422-425, 2003.
Osterburg, et al., "Highly antibiotic-resistant *Acinetobacter baumannii* clinical isolates are killed by the green tea polyphenol ( - )-epigallocatechin-3-gallate (EGCG)", Clinical Microbiology and Infection, vol. 15, No. 4, pp. 341-346, 2009.
Zheng, et al., "Fatty acid synthesis is target for antibacterial activity of unsaturated fatty acids", FEBS Letters, 2005, vol. 759, pp. 5157-5162.

* cited by examiner

MEMBRANE FUSION INHIBITOR

TECHNICAL FIELD

The present invention relates to an inhibitor that inhibits viral membrane fusion.

BACKGROUND ART

Infectious diseases caused by a number of different kinds of viruses such as influenza viruses and hepatitis viruses have been perceived as a problem, and various antiviral agents are under study. The virus propagation cycle is divided roughly into infection of viruses to cells, replication of the viruses in the infected cells, and release of propagated viruses to the outside of the infected cells. Approaches are being considered for each of these steps.

The virus propagation cycle will be explained briefly. First, a virus having an envelope identifies a sialic acid receptor on the surface of a cell and binds thereto. This triggers the endocytosis of the cell, and the virus is incorporated into the cell while being enclosed by a cell membrane. Then, when the inside of a phagosome enclosing the virus becomes acidic, by a membrane fusion activity of a membrane fusion protein (e.g., hemagglutinin (HA) or the like) present in the envelope, the membrane of the phagosome (derived from the cell) and the envelope of the virus (the membrane of the virus) fuse with each other. When this membrane fusion occurs, further by the action of a protein called M2, the membrane is perforated (uncoating), whereby RNA of the virus is released into the cell. The above-described process is a mechanism of infection of the virus to the cell. Next, a mechanism of replication and release of the virus in the infected cell will be described. The RNA of the virus released into the cell further is transported to a cell nucleus of the infected cell. Using this viral RNA, RNA, proteins, and the like that serve as components of new viruses are synthesized in a large quantity in the infected cell. Then, the virus genome and some of the proteins synthesized in the infected cell together form a virus core, which then moves to the cell membrane. Also, the synthesized membrane fusion protein and neuraminidase (NA) move to the cell membrane and bind thereto. Then, the virus that has moved to the cell membrane is packed with the cell membrane having the membrane fusion protein and NA, and then buds from the surface of the cell membrane. At this time, the budding virus binds to a sialic acid receptor present on the surface of the cell membrane of the infected cell. However, the budding virus is released to the outside of the cell when NA on the cell membrane cleaves the sialic acid receptor. The infection, replication, and release of the virus are performed in the above-described manner, and uninfected cells will be infected with the released viruses.

As antiviral agents, specifically, M2 inhibitors that approach the cell infection step (Non-Patent Document 1 and Non-Patent Document 2) and NA inhibitors that approach the replication and release step (Non-Patent Document 3 to Non-Patent Document 5) have been developed for influenza viruses, for example. The former are pharmaceutical compositions that inhibit the action of a protein M2 embedded in the envelope of a virus, and for example, hydrochloric acid amantadine is known. By these pharmaceutical compositions, the action of M2 is inhibited, whereby the uncoating of a virus in the infected cell is inhibited. Thus, there is no chance that RNA derived from the virus is transported to a cell nucleus, so that the synthesis of viral RNA and proteins itself can be blocked. On the other hand, the latter are pharmaceutical compositions that inhibit the action of NA present in the envelope of a virus, and for example, zanamivir (registered trademark "Relenza"), oseltamivir (oseltamivir phosphate; registered trademark "Tamiflu"), and the like are known. By these pharmaceutical compositions, the action of NA is inhibited, so that, even if the virus is replicated in the infected cell, NA cannot cleave the bonding between the budding virus and a sialic acid receptor. Thus, the budding virus cannot be separated from the membrane surface of the infected cell, and it eventually agglutinates.

However, the M2 inhibitors as the former are not effective against viruses lacking M2, such as influenza B viruses, and their side effects also are seen as a problem. Regarding the NA inhibitors as the latter, their high drug price and side effects are seen as problems. Furthermore, regarding either type of the antiviral agents, there is a concern about the development of viruses resistant thereto. In view of these circumstances, there is a demand for a pharmaceutical composition that targets a different step in the virus propagation cycle than conventional pharmaceutical compositions and also has excellent safety.

PRIOR ART DOCUMENTS

Non-Patent Document 1:

Zlydnikov, D. M. et al,; Study of rimantadine in the USSR: a review of the literature. Rev. Infect. Dis. 3, pp. 408-421, (1981).

Non-Patent Document 2:

Duff K. C. & Ashley R. H.; The transmembrane domain of influenza A M2 protein forms amantadine-sensitive proton channels in planar lipid bilayers. Virology 190, pp. 485-489, (1992).

Non-Patent Document 3:

Woods, J. M. et al,; 4-guanidino-2,4-dideoxy-2,3-dehydro-N-acetylneuraminic acid is a highly effective inhibitor both of the sialidase (neuraminidase) and of propagation of a wide range of influenza A and B viruses in vitro. Antimicrob. Agents Chemother. 37, pp. 1473-1479, (1993).

Non-Patent Document 4:

von Itzstein M. et al,; Rational design of potent sialidase-based inhibitors of influenza virus replication. Nature 363, pp. 418-423, (1993).

Non-Patent Document 5:

Kim C. U. et al,; Influenza neuraminidase inhibitors possessing a novel hydrophobic interaction in the enzyme active site. J. Am. Chem. Soc. 119, pp. 681-690, (1997).

BRIEF SUMMARY OF THE INVENTION

With the foregoing in mind, it is an object of the present invention to provide a pharmaceutical composition that is excellent in safety and targets a different step in the virus propagation cycle than conventional pharmaceutical compositions, applicable as an antiviral agent.

In order to achieve the above object, the present invention provides a membrane fusion inhibitor that inhibits viral membrane fusion. The membrane fusion inhibitor contains an epigallocatechin gallate (EGCG) derivative represented by the following chemical formula (1), an isomer thereof, or a salt thereof.

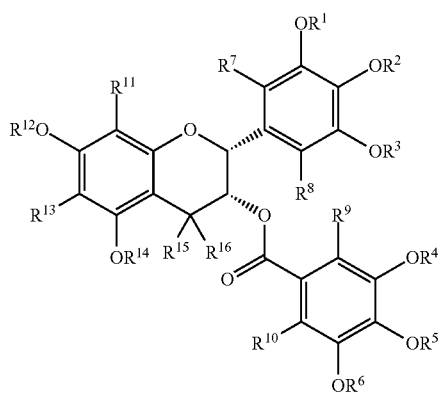

(1)

In the chemical formula (1), $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of the $R^1$ to $R^6$ is the acyl group. $R^7$ to $R^{16}$ are each a hydrogen atom, halogen, sodium, or potassium and may be identical to or different from one another.

The inventors of the present invention conducted a diligent study. As a result, they found that, unlike the M2 inhibitors and the NA inhibitors, EGCG and EGCG derivatives inhibit the membrane fusion caused by a membrane fusion protein, thereby achieving the present invention. According to the membrane fusion inhibitor of the present invention, in the above-described infection step in the virus propagation cycle, it is possible to inhibit the membrane fusion between the membrane of the phagosome enclosing the virus (derived from the cell) and the envelope of the virus (the membrane of the virus). Since the membrane fusion itself is inhibited as described above, steps downstream therefrom, i.e., the uncoating and the replication themselves can be blocked. Furthermore, since the membrane fusion inhibitor of the present invention targets a different step in the virus propagation cycle than conventional antiviral agents, it also can inhibit viral infection that cannot be blocked by the above-described M2 inhibitors and NA inhibitors, for example. Still further, in the EGCG derivative of the present invention, EGCG as the basic skeleton is, for example, catechin contained in tea and the like, and it is well known that catechin is excellent in safety. Also, the acyl group(s) of $R^1$ to $R^6$ has excellent safety. Therefore, it can be said that the membrane fusion inhibitor of the present invention is a pharmaceutical composition that also has excellent safety.

In the present invention, although the mechanism by which EGCG derivatives inhibit the membrane fusion caused by a membrane fusion protein of a virus is unknown, it is speculated that the acyl group(s) in an EGCG derivative delivers EGCG in the vicinity of a membrane fusion domain of the membrane fusion protein, thereby allowing the membrane fusion by a membrane fusion protein to be inhibited. It is to be noted, however, the present invention is by no means limited by this speculated mechanism.

DETAILED DESCRIPTION OF THE INVENTION

Figure 1:
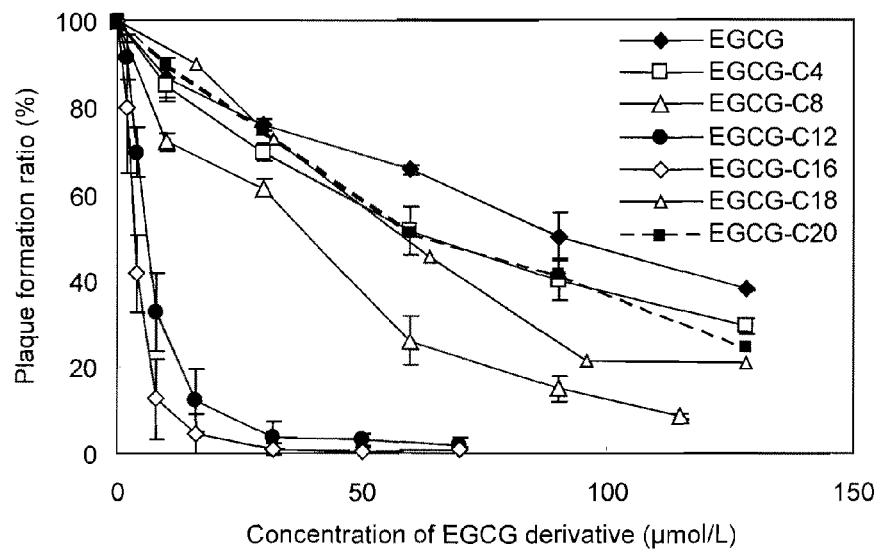
FIG. 1 is a graph showing the relationship between the concentration of EGCG derivatives and the plaque formation in Example 1 of the present invention.

The membrane fusion inhibitor of the present invention is, as described above, a membrane fusion inhibitor that inhibits viral membrane fusion, containing an epigallocatechin gallate derivative represented by the following chemical formula (1), an isomer thereof, or a salt thereof.

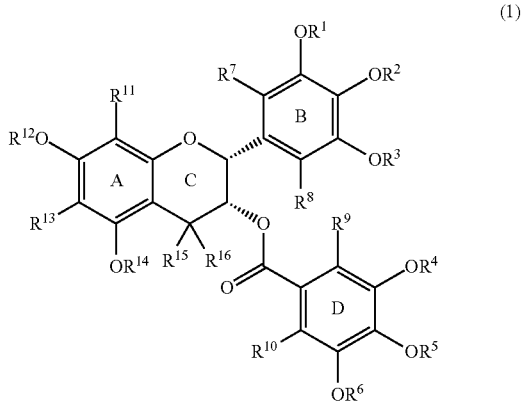

(1)

In the chemical formula (1), $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of the $R^1$ to $R^6$ is the acyl group. $R^7$ to $R^{16}$ are each a hydrogen atom, halogen, sodium, or potassium and may be identical to or different from one another.

In the chemical formula (1), "A to D" represent respective rings in epigallocatechin gallate. In the present invention, hereinafter, epigallocatechin gallate is referred to as "EGCG", and a derivative of EGCG is referred to as an "EGCG derivative".

In the present invention, the EGCG derivative include, for example, salts of compounds represented by the chemical formula (1), isomers, such as tautomers, stereoisomers, optical isomers, and geometric isomers, of the same, and mixtures of isomers. The salt is not particularly limited, and examples thereof include inorganic acid salts, organic acid salts, inorganic basic salts, organic basic salts, and acidic or basic amino acid salts. The isomer also can be purified by, for example, conventionally known separation methods such as various kinds of chromatography. Furthermore, in the present invention, the EGCG derivative also include, for example, compounds produced through metabolism, such as oxidation, reduction, hydrolysis, or conjugation, of the compounds represented by the chemical formula (1).

In $R^1$ to $R^6$, the main chain length of the acyl group is not particularly limited. For example, the main chain length of the acyl group is 2 to 20 atoms, preferably 4 to 20 atoms, more preferably 8 to 18 atoms, and still more preferably 12 to 16 atoms, including a carbon atom of a carbonyl group. It is to be noted that the main chain length of the acyl group refers to the number of atoms in the longest chain of the acyl group, and for example, not only a carbon atom but also a nitrogen atom, a sulfur atom, a phosphorus atom, an oxygen atom, a boron atom, a halogen atom, and the like may be contained therein.

In $R^1$ to $R^6$, the number of carbon atoms in the acyl group is not particularly limited. For example, the acyl group contains 2 to 20 carbon atoms, preferably 4 to 20 carbon atoms, more preferably 8 to 18 carbon atoms, and still more preferably 12 to 16 carbon atoms, including a carbon atom of a carbonyl group. It is more preferable that the number of carbon atoms is, for example, 4, 8, 12, 16, or 20, still more preferably 8, 12 or 16, and particularly preferably 12 or 16. When the acyl group further is substituted with the above-described substituent, it is preferable that the number of carbon atoms is, for example, the number excluding the number of carbon atoms in the substituent. Furthermore, the unsaturated acyl group may be either cis or trans, for example.

The acyl group is not particularly limited, and examples thereof include a formyl group (C1), an acetyl group (C2), a propionyl group (C3), a butyryl group (C4), an isobutyryl group (C4), a valeryl group (C5), an isovaleryl group (C5), a pivaloyl group (C5), a hexanoyl group (C6), an octanoyl group (C8), a geranoyl group (3,7-dimethylocta-2,6-dienoyl group) (C10), a trans-8-methyl-6-nonenoyl group (C10), an undecanoyl group (C11), a lauroyl group (dodecanoyl group) (C12), a tridecanoyl group (C13), a 12-(dimethylamino)lauroyl group (12-(dimethylamino)dodecanoyl group) (C14), a farnesoyl group (3,7,11-trimethyldodeca-2,6,10-trienoyl group) (C15), a palmitoyl group (hexadecanoyl group) (C16), a heptadecanoyl group (C17), a stearoyl group (octadecanoyl group) (C18), a linoleyl group (C18), a linolenyl group (C18), a nonadecanoyl group (C19), and an eicosanoyl group (icosanoyl group) (C20). Note here that the "C" in parentheses after each of the acyl groups listed above indicates the number of carbon atoms, including a carbon atom of a carbonyl group.

Among the above-listed acyl groups, for example, acyl groups represented by the following chemical formulae, and the like are particularly preferable. It is to be noted that the position of the unsaturated bond is not limited to those shown in the formulae below. Specifically, the unsaturated bond (double bond) in a trans-8-methyl-nonenoyl group (C10) is not limited to the 6-position shown in the formula below and may be any of the 2- to 5-positions and the 7-position, for example.

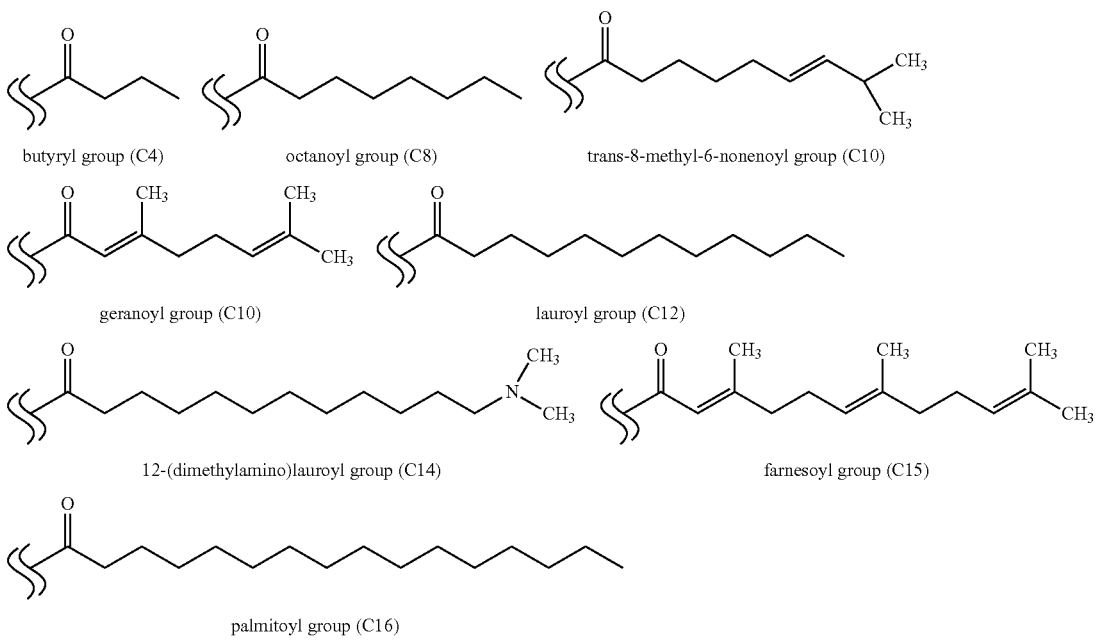

butyryl group (C4)

octanoyl group (C8)

trans-8-methyl-6-nonenoyl group (C10)

geranoyl group (C10)

lauroyl group (C12)

12-(dimethylamino)lauroyl group (C14)

farnesoyl group (C15)

palmitoyl group (C16)

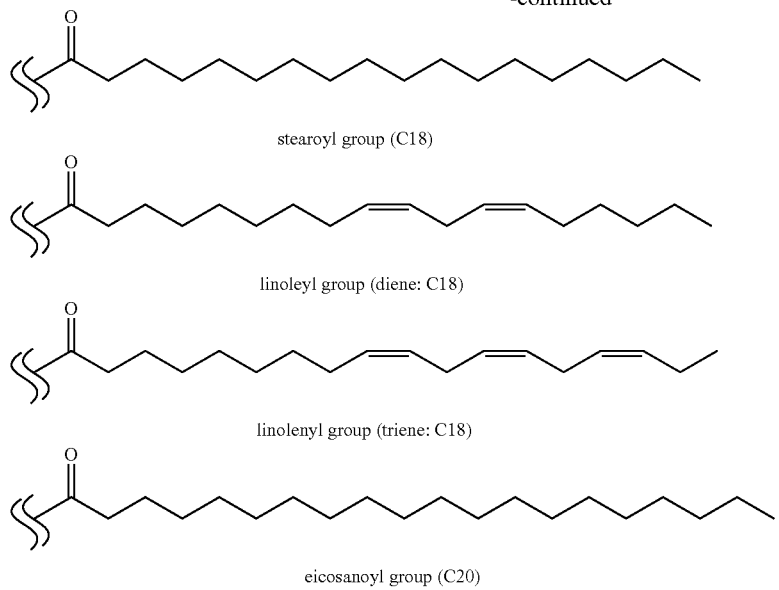

stearoyl group (C18)

linoleyl group (diene: C18)

linolenyl group (triene: C18)

eicosanoyl group (C20)

The kind of the acyl group is not particularly limited, and as described above, the acyl group may be either an unsaturated acyl group or a saturated acyl group. When the membrane fusion inhibitor is used to prevent viral infection to cells, among the acyl groups having, for example, the same main chain length, the unsaturated ones are preferable, and it is preferable that the number of unsaturated bonds therein is large. The number of unsaturated bonds in the acyl group is not particularly limited, and is, for example, 1 to 3, preferably 2 to 3. Furthermore, when the membrane fusion inhibitor is used against viruses prior to infection to cells, among the acyl groups having, for example, the same main chain length, the saturated ones are preferable.

In $R^1$ to $R^6$, the substituent is not particularly limited, and examples thereof include an alkyl group, an amino group, an alkylamino group, and a dialkylamino group.

The alkyl group may be, for example, a straight-chain or branched alkyl group having 1 to 6 carbon atoms and preferably is a methyl group. Furthermore, an alkyl group in the alkylamino group may be, for example, a straight-chain or branched alkyl group having 1 to 6 carbon atoms and preferably is a methylamino group. An alkyl group in the dialkylamino group may be, for example, a straight-chain or branched alkyl group having 1 to 6 carbon atoms and preferably is a dimethylamino group. They may be identical to or different from one another.

In the chemical formula (1), two or more of $R^1$ to $R^6$ may be the acyl groups, or only one of them may be the acyl group. In the former case, the acyl groups at the respective positions may be identical to or different from one another, for example. In the present invention, it is preferable that only one of $R^1$ to $R^6$ is the acyl group. In this case, other Rs are not particularly limited, and preferably are hydrogen atoms, for example.

In the chemical formula (1), among $R^1$ to $R^6$, the acyl group site is not particularly limited. For example, it is preferable that at least one of $R^1$ and $R^2$ in the B ring and $R^5$ and $R^6$ in the D ring has the acyl group, and it is particularly preferable that any one of $R^1$, $R^2$, $R^5$, and $R^6$ has the acyl group. In this case, other Rs are not particularly limited, and preferably are hydrogen atoms, for example.

Furthermore, in the chemical formula (1), it is preferable that at least one of $R^1$, $R^2$, and $R^3$ in the B ring is the acyl group, and it is more preferable that only one of $R^1$, $R^2$ and $R^3$ in the B ring is the acyl group. This is because EGCG derivatives with a modified B ring have, for example, higher metabolic stability.

In the chemical formula (1), $R^7$ to $R^{16}$ are each, as described above, a hydrogen atom, halogen, sodium, or potassium and may be identical to or different from one another. As shown by the following chemical formula (2), it is preferable that they are hydrogen atoms. In the following formula (2), for example, any of $R^1$ to $R^6$ may be the acyl group. Specifically, it is preferable that, for example, at least one of $R^1$ to $R^6$ or any one of $R^1$ to $R^6$ is the above-described acyl group, and it is more preferable that at least one of $R^1$, $R^2$, $R^5$, and $R^6$ or any one of $R^1$, $R^2$, $R^5$, and $R^6$ is the above-described acyl group. Among the acyl groups listed above, for example, a butyryl group, an octanoyl group, a trans-8-methyl-6-nonenoyl group, a geranoyl group, a lauroyl group, a 12-(dimethylamino)lauroyl group, a farnesoyl group, a palmitoyl group, a stearoyl group, a linoleyl group, a linolenyl group, and an eicosanoyl group are preferable.

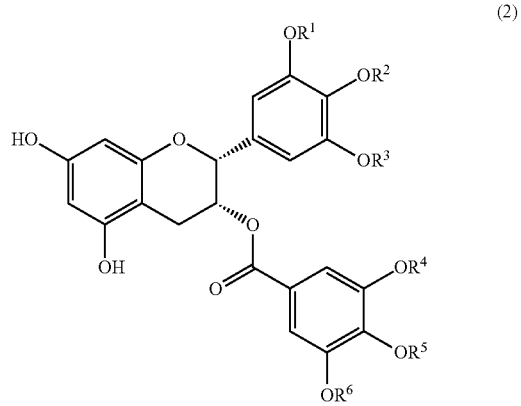

(2)

In the present invention, "halogen" refers to an arbitrary halogen element. Examples of the halogen include fluorine, chlorine, bromine, and iodine. Furthermore, in the present invention, an "alkyl group" is not particularly limited. Examples of the alkyl group include a methyl group, an ethyl group, an n-propyl group, an isopropyl group, n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same applies to a group containing an alkyl group in its structure or a group derived from an alkyl group (an alkylamino group, a dialkylamino group, an alkoxy group, a carboxyalkyl group, an alkoxycarbonylalkyl group, an alkoxyalkyl group, an alkenoxyalkyl group, or the like).

In the case where a substituent or the like is a group having a chain structure (e.g., an alkyl group, an alkylamino group, a dialkylamino group, an alkoxy group, a carboxyalkyl group, an alkoxycarbonylalkyl group, an alkoxyalkyl group, an alkenoxyalkyl group, or the like), it may have either a straight-chain or branched structure, unless otherwise limited. The same applies to the case where a chain structure is contained in a part of a substituent or the like, e.g., the case where a chain structure is contained in a substituent in a substituted alkyl group, a substituted aryl group, or the like. In the case where a substituent or the like has isomers, the substituent may be any of the isomers unless otherwise limited. For example, when it is simply referred to as a "propyl group", it may be either an n-propyl group or an isopropyl group. When it is simply referred to as a "butyl group", it may be any of an n-butyl group, an isobutyl group, a sec-butyl group, and a tert-butyl group. When it is simply referred to as a "naphthyl group", it may be either a 1-naphthyl group or a 2-naphthyl group.

In the present invention, for example, only one kind of EGCG derivative may be used, or two or more kinds of EGCG derivatives may be used in combination. For example, two or more kinds of EGCG derivatives having acyl groups at different sites among $R^1$ to $R^6$ may be used, or two or more kinds of EGCG derivatives having different acyl groups may be used. Specifically, it is possible to use a mixture of two or more kinds selected from an EGCG derivative in which $R^1$ in the B ring is the acyl group, an EGCG derivative in which $R^2$ in the B ring is the acyl group, and an EGCG derivative in which $R^3$ in the B ring is the acyl group, or a mixture of all the three kinds of them. Alternatively, it also is possible to use a mixture of two or more kinds selected from an EGCG derivative in which $R^4$ in the D ring is the acyl group, an EGCG derivative in which $R^5$ in the D ring is the acyl group, and an EGCG derivative in which $R^6$ in the D ring is the acyl group, or a mixture of all the three kinds of them. Furthermore, it is possible to use a mixture of an EGCG derivative in which at least one of $R^1$ to $R^3$ in the B ring is the acyl group and an EGCG derivative in which at least one of $R^4$ to $R^6$ in the D ring is the acyl group.

Viruses to which the membrane fusion inhibitor of the present invention is applied are not particularly limited, and examples thereof include influenza viruses, Semliki Forest viruses, and HIV-1. The type of viruses is not particularly limited, and examples thereof include influenza A, B, and C viruses. Influenza A viruses are not particularly limited, and examples thereof include H1N1, H5N1, and H3N2. Furthermore, examples of influenza B viruses include Influenza B/Yamanashi/166/98. Furthermore, examples of the influenza viruses include mammalian infectious influenza viruses and avian infectious influenza viruses. The EGCG derivative of the present invention is, as described above, a membrane fusion inhibitor that inhibits the membrane fusion between a virus incorporated into a cell and the cell, unlike conventional antiviral agents that target NA or M2. Accordingly, it is particularly effective against viruses lacking NA (e.g., influenza C viruses and the like), viruses resistant to NA inhibitors, viruses lacking M2 (e.g., influenza B viruses and the like), viruses resistant to M2 inhibitors such as amantadine, and the like.

It is only necessary that the membrane fusion inhibitor of the present invention contains the EGCG derivative, and the form of the membrane fusion inhibitor is by no means limited. The membrane fusion inhibitor may be in the form of liquid such as a solution or a dispersion, solid, powder, or the like, for example. Furthermore, the dosage form is not particularly limited, and can be set as appropriate depending on, for example, the administration method. Examples of the dosage form include a liquid medicine, a capsule, a tablet, granules (microgranules), and a powder medicine. The administration method is not particularly limited, and examples thereof include oral administration and parenteral administration. Examples of the parenteral administration include transdermal administration, intraperitoneal administration, intravenous administration such as intravenous injection, intramuscular administration, subcutaneous administration such as subcutaneous injection, and rectal administration. The transdermal administration is preferable. The membrane fusion inhibitor of the present invention can be administered as, for example, an oral medicine, a sublingual formulation, a nasal drop, a gargle, a topical cream, or the like containing the EGCG derivative depending on, for example, the administration form. It also can be administered as the EGCG derivative, or a solution or dispersion containing the same using a syringe, a nebulizer, an aspirator, or the like. Furthermore, it can be administered as the EGCG derivative or powder containing the same using a nebulizer, an aspirator, or the like, for example. Moreover, because the membrane fusion inhibitor of the present invention can lower the infectivity of viruses, it may be in the form of a cleaner, such as a hand-wash or a wiping agent, containing the EGCG derivative, for example. By treating a place where it is considered that viruses are present, e.g., hands, a desk, or the like, with the membrane fusion inhibitor of the present invention in such a form, it is possible to lower the infectiousness of the viruses present in the place so as to prevent viral infection. Also, the membrane fusion inhibitor of the present invention may be carried in a mask.

The membrane fusion inhibitor of the present invention can be used for prevention and treatment of viral infection, for example. Examples of a subject to which the membrane fusion inhibitor of the present invention is administered include mammals such as humans, pigs, ferrets, rats, mice, and cows, and birds such as ducks and chickens.

In the membrane fusion inhibitor of the present invention, the content of the EGCG derivative is not particularly limited, and can be determined as appropriate depending on, for example, the purpose of administering it or its administration method. In the case where the membrane fusion inhibitor of the present invention is a gargle, it is preferable that 20 to 2000 nmol/l of the EGCG derivative is contained per single dose, for example. In the case where the membrane fusion inhibitor of the present invention is a nasal drop, for example, it is preferable that 20 to 2000 nmol/l of the EGCG derivative is contained per single dose.

The membrane fusion inhibitor of the present invention further may contain an additive, a base, and the like as appropriate depending on, for example, its dosage form or administration method. Examples of the additive include an excipient, a bonding agent, a lubricant, a disintegrant, a coloring agent, a taste masking agent, an odor masking agent, an emulsifying agent, a surfactant, a solubilizing agent, a suspending agent, a tonicity agent, a buffer, an antiseptic agent, an antioxidant agent, a stabilizing agent, and an absorption promoter. The proportion of each of these additives to be added is not particularly limited. They can be added within the range in which they do not reduce the effect of the EGCG derivative.

Next, an expression inhibitor of the present invention is an expression inhibitor that inhibits expression of a protein of viruses and contains the above-described EGCG derivative. The expression inhibitor of the present invention is characterized in that it contains the EGCG derivative. Other configurations, the form, the use method, etc. of the expression inhibitor are not limited, and may be the same as described above for the membrane fusion inhibitor. According to the EGCG derivative of the present invention, when, for example, a cell is infected with a virus, it is possible to suppress the expression of a protein of the virus in the cell. Thus, it is possible to inhibit a stage before the virus propagates in the infected cell. It is to be noted that, in the expression inhibitor of the present invention, the mechanism by which it exhibits the expression-inhibiting effect is not particularly limited. For example, it is not limited to the mechanism by which the membrane fusion is inhibited as described above.

Next, an antiviral agent of the present invention is characterized in that it contains the membrane fusion inhibitor of the present invention. It is only necessary that the antiviral agent of the present invention contains the membrane fusion inhibitor of the present invention, and other configurations are by no means limited. Furthermore, the form and the use method of the antiviral agent of the present invention are the same as described above. Furthermore, it is only necessary that the antiviral agent of the present invention contains the EGCG derivative, and the mechanism by which it exhibits the antiviral effect is not particularly limited. For example, it is not limited to the mechanism by which the membrane fusion is inhibited as described above.

Viruses to which the antiviral agent of the present invention is applied is not particularly limited, and examples thereof include those described above. Among them, the antiviral agent of the present invention preferably is applied to viruses lacking NA, viruses resistant to NA inhibitors, viruses lacking M2, viruses resistant to M2 inhibitors, and the like for the same reason as described above.

The antiviral agent of the present invention further may contain an M2 inhibitor. The mechanism by which the membrane fusion inhibitor of the present invention is involved in viral infection is different from the mechanism by which the M2 inhibitor is involved in the same. Therefore, when the antiviral agent of the present invention contains the membrane fusion inhibitor of the present invention and the M2 inhibitor, the former inhibits the membrane fusion of a virus, and even if the membrane fusion occurs, the latter blocks the uncoating, thereby achieving two-stage inhibition of viral infection. Also, the antiviral agent of the present invention further may contain an NA inhibitor. When the antiviral agent of the present invention contains the membrane fusion inhibitor of the present invention and the NA inhibitor, the former inhibits the membrane fusion of a virus to block the replication, and even if the virus is replicated, the latter blocks the release of the replicated viruses, thereby achieving inhibition of two stages, namely, the viral infection and the release of the replicated viruses.

The method of producing the EGCG derivative in the present invention is not particularly limited. As the method, a conventionally known method such as an organic synthesis method or a chemical synthesis method utilizing an enzyme or the like can be employed, for example. The chemical synthesis method utilizing an enzyme is not particularly limited, and examples thereof include a method utilizing a lipase, disclosed in WO 2007/105280. Specifically, this is a method in which an enzyme reaction of EGCG and an acyl group donor as substrates with a lipase is caused in an organic solvent to acylate the EGCG. According to this method, for example, it is possible to acylate EGCG selectively. One example of a method using a lipase will be given below. It should be noted, however, the present invention is by no means limited by the method of producing an EGCG derivative.

As the lipase, lipase of IUB No. 3.1.1.3. can be used, for example. Specific examples thereof include: lipases derived from the genus *Aspergillus*, such as *Aspergillus niger*; lipases derived from the genus *Candida*, such as *Candida rugosa*, *Candida cylindracea*, and *Candida antarctica*; lipases derived from the genus *Pseudomonas*, such as *Pseudomonas fluorescens*, *Pseudomonas cepacia*, and *Pseudomonas stutzerzi*; lipases derived from the genus *Alcaligenes*; lipases derived from the genus *Burkholderia*, such as *Burkholderia cepacia*; and lipases derived from porcine pancreas. They can be prepared by conventionally known methods. However, it also is possible to use commercially available products such as, for example, Lipase AS "AMANO", Lipase AYS "AMANO", Lipase PS "AMANO", Lipase AK "AMANO" 20, Lipase AH "AMANO" (all trade names: Amano Enzyme Inc.), Lipase MY, Lipase OF, Lipase PL, Lipase PLC, Lipase PLG, Lipase QLM, Lipase QLC, Lipase QLG, Lipase SL, Lipase TL (all trade names: Meito Sangyo Co., Ltd.), Lipase PPL, L4777 Lipase acrylic resin from *Candida Antarctica*, L3126 Lipase from porcine pancreas (all trade names: Sigma-Aldrich Co.), and the like. The physicochemical properties of the respective commercially available products are as described in their product manuals, and enzymes having similar physicochemical properties also can be used.

Also, the lipase may be the one having physicochemical properties and enzymological properties shown in any one of the following items (1) to (8).
(1) molecular weight: 35,000, isoelectric point: 4.10 (e.g., a lipase derived from *Aspergillus niger*)
(2) molecular weight: 64,000, isoelectric point: 4.30, inactivated by the treatment at 80° C. for 10 minutes (e.g., a lipase derived from *Candida rugosa*)
(3) optimum pH: 8, optimum temperature: 60° C., particularly stable at a pH in the range from 4 to 10, particularly stable at 70° C. or lower (e.g., a lipase derived from *Pseudomonas fluorescens*)
(4) molecular weight: 60,000, optimum pH: 6 to 7, pH stability: 3 to 8, optimum temperature: 40° C. to 50° C., particularly stable in the form of a solution at 37° C. or lower (e.g., a lipase derived from *Candida cylindracea*, a lipase derived from *Candida rugosa*)
(5) molecular weight: 30,000, isoelectric point: 4.5, optimum pH: 8 to 9.5, pH stability: 7 to 10, optimum temperature: 50° C., particularly stable at 40° C. or lower (e.g., a lipase derived from the genus *Alcaligenes*)
(6) molecular weight: 31,000, isoelectric point: 4.9, optimum pH: 7 to 9, pH stability: 6 to 10, optimum temperature: 65° C. to 70° C., particularly stable at 50° C. or lower (e.g., a lipase derived from the genus *Alcaligenes*)

(7) molecular weight: 31,000, isoelectric point: 5.2, optimum pH: 7 to 9, pH stability: 6 to 10, optimum temperature: 65° C. to 70° C., particularly stable at 60° C. or lower (e.g., a lipase derived from *Pseudomonas cepacia*, a lipase derived from *Burkholderia cepacia*)

(8) molecular weight: 27,000, isoelectric point: 6.6, optimum pH: 7 to 8, pH stability: 6 to 9, optimum temperature: 50° C., particularly stable at 40° C. or lower (e.g., a lipase derived from *Pseudomonas stutzen*)

The organic solvent is not particularly limited, and acetonitrile, acetone, dimethylformamide (DMF), dimethyl sulfoxide (DMSO), or the like can be used, for example. Also, it may be, for example, an organic solvent with a parameter indicating the hydrophobicity (log P value) in the range from −0.35 to 0.28. Examples of such an organic solvent include the above-described acetonitrile (log P value: −0.45 to 0.19), acetone (log P value: −0.16 to 0.19), DMF (log P value: −1.01 to 0.28), and DMSO (log P value: −1.35 to 0.28). Other than these, conventionally known solvents satisfying the above-described parameter also can be used. Since the logP is a value specific to each solvent, those skilled in the art can select a solvent satisfying the above-described parameter. Note here that the log P is a value determined by adding a target substance to a mixed solution of octanol and water, determining the ratio of the concentrations of the target substance in the octanol layer and the concentration of the same in the water layer when the octanol and the water come to equilibrium, and indicating the ratio by common logarithm. As described above, the log P is common as a parameter indicating the hydrophobicity of a substance.

In the present invention, examples of an acyl group (R—CO—) donor include carboxylic acid vinyl ester (R—CO—O—CH=CH$_2$). Examples of the acyl group include straight-chain or branched, saturated or unsaturated acyl groups such as described above.

When DMF is used in the enzyme reaction solution, the proportion of the added EGCG is not particularly limited, and is, for example, 0.2 to 100 mmol/l, preferably 0.5 to 50 mmol/l, and more preferably 0.5 to 20 mmol/l. The proportion of the added acyl group donor is not particularly limited, and can be determined as appropriate depending on, for example, the proportion of the added EGCG in the reaction solution. Specifically, the proportion (molar ratio) of the added EGCG and acyl group donor is, for example, 1:1 to 1:10, preferably 1:1 to 1:5, and more preferably 1:1 to 1:3. Furthermore, the proportion of the added lipase in the reaction solution can be determined as appropriate depending on, for example, the proportions of the added EGCG and acyl group donor, the specific activity of the lipase, or the like, and is not particularly limited. However, it is, for example, 500 to 50,000 U/l, preferably 500 to 5,000 U/l, and more preferably 1,000 to 2,500 U/l with respect to 1 mmol/l of the EGCG, for example.

The conditions for the enzyme reaction are not particularly limited, and the reaction temperature is, for example, in the range from 45° C. to 75° C. The reaction time can be determined as appropriate depending on, for example, the amounts of the substrates and the enzyme, and is not particularly limited. It is, for example, 30 minutes to 24 hours (1440 minutes), preferably 1 hour (60 minutes) to 3 hours (180 minutes), and more preferably 1.5 hours (90 minutes) to 3 hours (180 minutes).

To the reaction solution, a basic catalyst further may be added. Examples of the basic catalyst include pyridine and tertiary amine such as triethylamine. The proportion of the added basic catalyst in the reaction solution is not particularly limited, and is, for example, 5 to 720 mmol/l, preferably 12 to 240 mmol/l, and more preferably 12 to 48 mmol/l.

In EGCG, the position to which the acyl group is introduced can be selected by the kind of the lipase to be used, for example. Furthermore, the number of acyl groups to be introduced into EGCG can be determined by the kind of the organic solvent to be used and the reaction time, for example. For example, as the hydrophobicity of the organic solvent becomes relatively higher (as the hydrophilicity of the organic solvent becomes relatively lower), the number of acyl groups to be introduced can be made relatively smaller, and as the hydrophilicity of the organic solvent becomes relatively higher (as the hydrophobicity of the organic solvent becomes relatively lower), the number of acyl groups to be introduced can be made relatively larger. Also, by using a mixture of two or more kinds of organic solvents, it is possible to adjust the number of acyl groups to be introduced. Specifically, for example, in the case where one acyl group is to be introduced, acetonitrile or the like preferably is used; for example, in the case where one to two acyl groups are to be introduced, acetone, acetonitrile, or the like preferably is used; and for example, in the case where three to five acyl groups are to be introduced, DMSO, DMF, or the like preferably is used.

Moreover, even when the organic solvent to be used is the same, it is also possible to adjust the number of acyl groups to be introduced by controlling the reaction time or the reaction temperature, for example. This will be exemplified below. However, it should be noted that the present invention is not limited thereto. When DMF is used, by setting the reaction temperature within the range from about 57° C. to about 70° C. and the reaction time to be long (e.g., about 3 to 5 hours), for example, a derivative in which two acyl groups selectively are introduced to EGCG can be obtained preferentially. On the other hand, by lowering the reaction temperature (e.g., to a temperature about 5° C. lower than 57° C.) and shortening the reaction time (e.g., about 1 to 3 hours), one acyl group can be introduced selectively. Also, by using a mixed solvent of the same amount (weight) of acetone and DMF, one acyl group can be introduced selectively to EGCG.

Furthermore, the number of acyl groups to be introduced can be increased by adding the above-described basic catalyst to the reaction solution. In this case, the site in EGCG to which an acyl group(s) further is introduced is determined depending on the position selectivity of the lipase, for example.

The yield of the EGCG derivative by the enzyme reaction can be improved relatively by, for example, setting the reaction temperature relatively high. As described above, the reaction temperature generally is 45° C. to 75° C. However, from the viewpoint of improving the yield, it preferably is 57° C. to 75° C., more preferably 57° C. to 70° C. In particular, when the reaction temperature is 57° C. to 70° C., it is possible to realize about 35% to 45% of the yield of the EGCG-acylated derivative. Note here that the yield means the proportion of an EGCG-acylated derivative (e.g., total monoacylated derivative) calculated assuming that EGCG used in the reaction is 100% (i.e., the conversion efficiency).

In the present invention, as described above, one kind of EGCG derivative may be used or a mixture of two or more kinds of EGCG derivatives may be used, for example. When isolating one kind of EGCG derivative from the mixture, it can be achieved by, for example, a conventionally known method using chromatography or the like.

Next, a method for inhibiting infection according to the present invention is a method for inhibiting viral infection, including administering the above-described EGCG derivative to a subject. The present invention is characterized in that it uses the EGCG derivative, and configurations, conditions, etc. other than this are by no means limited. The EGCG derivative, the use method thereof, etc. are the same as described above, for example. In the present invention, for example, the membrane fusion inhibitor, expression inhibitor, antiviral agent of the present invention, or the like may be administered as the EGCG derivative.

In the present invention, the subject is by no means limited, and examples thereof include mammals such as humans, pigs, ferrets, rats, mice, and cows and birds such as ducks and chickens. Furthermore, the subject may be a living organism itself or may be a cell or a tissue collected from a living organism, or a culture thereof, for example.

When the subject is a living organism, the administration method is not particularly limited, and examples thereof include parenteral administration and oral administration. Examples of the parenteral administration include transdermal administration, intraperitoneal administration, intravenous administration, intramuscular administration, subcutaneous administration, and rectal administration, and transdermal administration is preferable. In the case of the parenteral administration, the EGCG derivative can be administered by way of oral administration, nasal administration, gargling, or injection, or with the use of a nebulizer, an aspirator, or the like, for example. Furthermore, examples of the transdermal administration method include hand-washing with a cleaner containing the EGCG derivative and wiping with a wiping agent or the like containing the EGCG derivative.

Furthermore, when the subject is a cell, a tissue, or the like collected from a living organism, the administration method is not particularly limited, and can be addition to a medium or the like, for example.

The timing of administrating the EGCG derivative to the subject is not particularly limited, and may be either before or after viral infection, for example. As described above, EGCG derivatives can block an early stage of viral infection by inhibiting the propagation of virus proteins in infected cells and the membrane fusion mediated by virus-derived membrane fusion proteins, for example. Thus, the present invention also can be referred to as, for example, a method of inhibiting expression of virus proteins in infected cells or a method of inhibiting viral membrane fusion.

EXAMPLES

Next, the present invention will be described with reference to examples. It is to be noted, however, the present invention is by no means limited by the following examples.

Example 1

(1) Preparation of EGCG Derivatives

As membrane fusion inhibitors, EGCG derivatives were prepared in the following manner.

100 ml of DMF, 1 g of EGCG, 927 mg of each type of acyl group donors shown below, and 50000 U of lipase (trade name "Lipase PL", Meito Sangyo Co., Ltd.) were mixed together. The resultant mixture was incubated at 57° C. for 2 hours to cause an enzyme reaction.

TABLE 1

| | | | Acyl group | |
|---|---|---|---|---|
| | Acyl group donor | Acyl group | Carbon number | Main chain length |
| No. 1 | vinyl butyrate | butyryl | C4 | 4 |
| No. 2 | vinyl octanoate | octanoyl | C8 | 8 |
| No. 3 | trans-8-methyl-6-vinyl nonenoate | trans-8-methyl-6-nonenoyl | C10-Trans | 9 |
| No. 4 | vinyl laurate | lauroyl | C12 | 12 |
| No. 5 | vinyl farnesylate | farnesoyl | C15-Far | 12 |
| No. 6 | vinyl palmitate | palmitoyl | C16 | 16 |
| No. 7 | vinyl stearate | stearoyl | C18 | 18 |
| No. 8 | vinyl linoleate | linoleyl (diene) | C18-DE | 18 |
| No. 9 | α-vinyl linolenate | linolenyl (triene) | C18-TE | 18 |
| No. 10 | vinyl eicosanoate | eicosanoyl | C20 | 20 |

Then, the reaction solution having undergone the incubation was filtered and concentrated, after which it was applied to column chromatography (spherical, neutral, 40-50 μm, trade name "Silica gel N60", KANTO CHEMICAL CO., INC.) to remove unreacted acyl group donors as impurities. The thus-obtained reaction product was subjected to electrospray ionization mass spectrometry (ESI-MS). As a result, it was found that one acyl group shown in Table 1 was introduced via an ester bond in $R^1$ or $R^2$ in the B ring or $R^5$ or $R^6$ in the D ring of the EGCG.

Furthermore, in order to identify which position of the EGCG was esterified, the reaction product was analyzed by proton nuclear magnetic resonance ($H^1$ NMR). The result thereof is shown in the following table.

TABLE 2

| | | B ring | | D ring | | |
|---|---|---|---|---|---|---|
| | | $R^1$ | $R^2$ | $R^5$ | $R^6$ | |
| | | Position | | | | |
| | Acyl group | 3 | 4 | 4 | 5 | B/D* |
| No. 1 | C4 butyryl | 35 | 44 | 8 | 12 | 79/21 |
| No. 2 | C8 octanoyl | 35 | 39 | 6 | 20 | 74/26 |
| No. 3 | C10-Trans trans-8-methyl-6-nonenoyl | 13 | 21 | 14 | 52 | 34/66 |
| No. 4 | C12 lauroyl | 30 | 39 | 9 | 22 | 69/31 |
| No. 5 | C15-Far farnesoyl | 11 | 4 | 13 | 72 | 15/85 |
| No. 6 | C16 palmitoyl | 38 | 35 | 7 | 20 | 73/27 |
| No. 7 | C18 stearoyl | 38 | 35 | 7 | 20 | 73/27 |
| No. 8 | C18-DE linoleyl | 28 | 22 | 5 | 45 | 50/50 |
| No. 9 | C18-TE linolenyl | 15 | 19 | 4 | 62 | 34/66 |
| No. 10 | C20 eicosanoyl | 38 | 36 | 8 | 19 | 73/27 |

*Ratio between B ring-esterified EGCG derivative and D ring-esterified EGCG derivative EGCG derivatives in which the acyl groups No. 1 to No. 10 respectively were introduced hereinafter referred to as EGCG-C4 (EGCG-But), EGCG-C8 (EGCG-Oct), EGCG-C12 (EGCG-Lau), EGCG-C16 (EGCG-Pal), EGCG-C18 (EGCG-Ste), EGCG-C20 (EGCG-Eic), EGCG-C18-DE (EGCG-linoleyl), EGCG-C18-TE (EGCG-linolenoyl), EGCG-C15-Far (EGCG-Far), and EGCG-C10-Trans (EGCG-Trans), respectively. These EGCG derivatives are EGCG derivatives shown by the chemical formula (2), and each of the above-described sites ($R^1$, $R^2$, $R^5$, or $R^6$) is an acyl group represented by the structural formula shown in Table 2. Using these EGCG derivatives, the following experiment was conducted.

(2) Prevention of Viral Infection to Cells

The EGCG derivatives were dissolved in Opti-MEM (0.2% DMSO), respectively, so as to achieve predetermined concentrations from 0 to 128 μM (μmol/l). Thus, various sample solutions were prepared (No. 1 to No. 10). On the other hand, on a 6-well plate filled with a culture solution, canine kidney cultured cells (MDCK) were cultured until confluent (about 8 hours). The culture solution was removed from the plate, and the cultured cell sheets were washed with D-PBS. Thereafter, 1.2 ml of each of the sample solutions was applied to the cell sheet, and in the presence of $CO_2$, they were incubated at 37° C. for 2 hours. The sample solution then was removed, and the cell sheet was washed with D-PBS. Thereafter, influenza viruses (A/PR8/34/H1N1) suspended with DMEM (0.2% BSA) were applied to the cell sheet at an MOI of $2.5 \times 10^{-4}$. Then, the cell sheet was incubated at room temperature for 1 hour, after which 0.8% agarose gel containing $6.0 \times 10^{-4}$% trypsin and 0.2% BSA was layered on the cell sheet. The cell sheet further was incubated at 37° C. for 52 to 60 hours in the presence of $CO_2$, and thereafter, the number of plaques appearing on the cell sheet was counted. Assuming that the number of plaques on the cell sheet to which no EGCG derivative had been added (0 μmol/l) was 100, the plaque formation ratio (%) was calculated. As a comparative example, the same treatment was carried out using EGCG to which no acyl group was introduced, instead of the EGCG derivatives. FIG. 1 shows the results obtained with regard to the EGCG derivatives No. 1 to No. 6 and the EGCG. FIG. 1 is a graph showing the relationship between the concentration of the EGCG derivatives and the plaque formation ratio. In FIG. 1, the plaque formation ratio is indicated as a relative value (%) assuming that the number of plaques obtained when no EGCG derivative was added (0 μmol/l) was 100% (The same applies hereinafter). Also, with regard to the EGCG derivatives No. 1 to No. 10 and the EGCG, the antiviral activity ($EC_{50}$), cytotoxicity ($CC_{50}$), and SI are shown in the following table.

TABLE 3

Viral infection-preventing effect

| | Membrane fusion inhibitor | $EC_{50}$*1 (μmol/l) | $CC_{50}$*2 (μmol/l) | SI*3 |
|---|---|---|---|---|
| Comparative example | EGCG | 94.60 (±11.1) | 275.5 (±6.0) | 2.91 |
| Example No. 1 | EGCG-C4 | 63.70 (±4.0) | 309.0 (±4.0) | 4.85 |
| No. 2 | EGCG-C8 | 39.00 (±3.1) | 195.0 (±9.0) | 5.01 |
| No. 4 | EGCG-C12 | 5.81 (±0.83) | 42.0 (±3.9) | 7.23 |
| No. 5 | EGCG-C15-Far | 4.0 (±0.5) | 24.0 (±3.0) | 6.0 |
| No. 6 | EGCG-C16 | 4.02 (±0.48) | 86.2 (±12.5) | 21.40 |
| No. 7 | EGCG-C18 | 64.0 (±0.5) | 300.0 (±25.0) | 4.68 |
| No. 8 | EGCG-C18-DE | 7.0 (±0.5) | 250.0 (±25.0) | 35.7 |
| No. 9 | EGCG-C18-TE | 3.0 (±0.5) | 32.0 (±3.5) | 10.6 |
| No. 10 | EGCG-C20 | 66.90 (±8.3) | 318.0 (±55.0) | 4.75 |

*1 Antiviral effect (50% effective concentration)
*2 Cytotoxicity (50% cytotoxic concentration)
*3 Selectivity (Selective Index = $CC_{50}/EC_{50}$)

As can be seen from FIG. 1, by adding each of the EGCG derivatives to the cells ahead of time, plaque formation was reduced as compared with the case where the EGCG was added (filled diamond). In particular, marked reduction was observed in the cases where EGCG-16 and EGCG-C12 were used. Furthermore, as can be seen from Table 3, by adding each of the EGCG derivatives to the cells ahead of time, the antiviral effect stronger than that of EGCG in the comparative example was obtained. Moreover, there were no problems regarding the cytotoxicity. In particular, each of EGCG-12, EGCG-C15-Far, EGCG-16, ECGC-C18-DE, and EGCG-C18-TE had an $EC_{50}$ in the range from 3 to 7 and thus exhibited an antiviral effect much stronger than that of the EGCG, which had an $EC_{50}$ of 94.60. Among them, EGCG-C18-DE had a low $EC_{50}$ and a high $CC_{50}$. This demonstrates that EGCG-C18-DE exhibits an excellent antiviral effect at a low concentration and also has very low toxicity. Also, it was found that EGCG-C18-TE exhibits an excellent antiviral effect at a very low concentration. Still further, from the comparison between EGCG-C12 and EGCG-C15-Far having the same main chain length (12), it was demonstrated that the one having an unsaturated bond exhibits a stronger antiviral effect. Similarly, from the comparison among EGCG-C18, EGCG-C18-DE, and EGCG-C18-TE having the same main chain length (18), it was demonstrated that the one having an unsaturated bond exhibits a stronger antiviral effect and the antiviral effect becomes stronger as the number of unsaturated bonds increases. As described above, from the fact that excellent antiviral effects were exhibited by adding the EGCG derivatives to the cells ahead of time, it can be said that the membrane fusion inhibitor of the present invention can be used as an agent for preventing viral infection.

(3) Inhibition of Viral Infectivity

Figure 2:
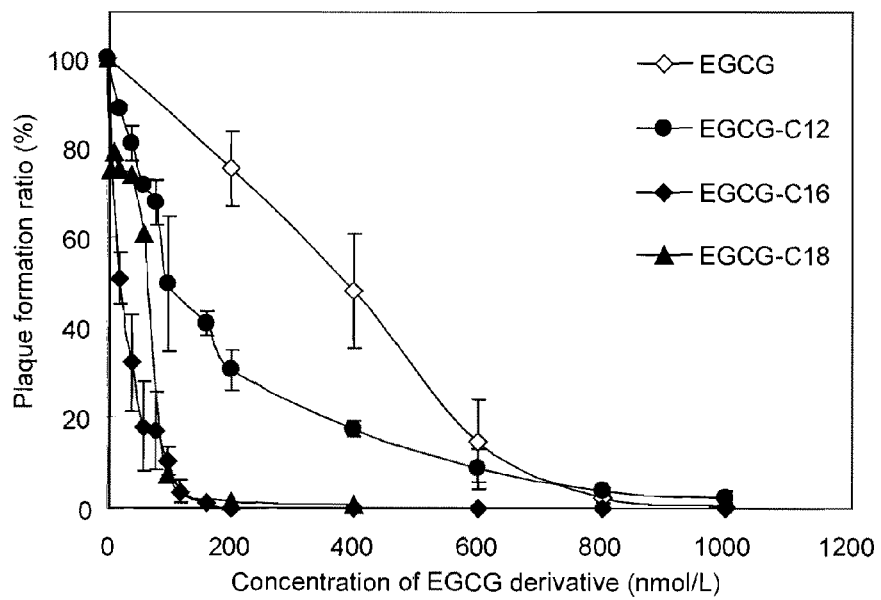
FIG. 2 is a graph showing the relationship between the concentration of EGCG derivatives and the plaque formation in Example 1 of the present invention.

The various EGCG derivatives were dissolved in Opti-MEM (0.2% DMSO), respectively, so as to achieve predetermined concentrations (0 to 10000 nmol/l), and influenza viruses (A/PR8/34/H1N1) further were added thereto. The resultant mixtures were incubated at room temperature for 30 minutes. On a 6-well plate filled with a culture solution, canine kidney cultured cells (MDCK) were cultured until confluent (about 8 hours). The culture solution was removed from the plate, and the cultured cell sheets were washed with D-PBS. Thereafter, each of sample solutions containing the above-described respective EGCG derivatives and influenza viruses was applied to the cell sheet so that the MOI of the influenza viruses would be $2.5 \times 10^{-4}$. Then, the cell sheet was incubated at room temperature for 1 hour, after which 0.8% agarose gel containing $6.0 \times 10^{-4}$% trypsin and 0.2% BSA was layered on the cell sheet. The cell sheet further was incubated at 37° C. for 52 to 60 hours in the presence of $CO_2$, and thereafter, the number of plaques appearing on the cell sheet was counted. Assuming that the number of plaques on the cell sheet to which no EGCG derivative had been added (0 μmol/l) was 100, the plaque formation ratio (%) was calculated. As a comparative example, the same treatment was carried out using EGCG to which no acyl group was introduced, instead of the EGCG derivatives. The result thereof is shown in FIG. 2. FIG. 2 is a graph showing the relationship between the concentration of the EGCG derivatives and the plaque formation ratio. Also, with regard to the EGCG derivatives and the EGCG, the antiviral effect ($EC_{50}$) and SI were shown in the following table.

TABLE 4

Viral infectivity-inhibiting effect

| | Membrane fusion inhibitor | $EC_{50}$*1 (μmol/l) | SI*2 |
|---|---|---|---|
| Comparative example | EGCG | 0.391 (±0.056) | 703 |
| Example No. 3 | EGCG-C10-Trans | 0.300 (±0.050) | 833 |
| No. 4 | EGCG-C12 | 0.118 (±0.023) | 353 |
| No. 6 | EGCG-C16 | 0.020 (±0.007) | 4230 |
| No. 7 | EGCG-C18 | 0.060 (±0.010) | 5000 |
| No. 8 | EGCG-C18-DE | 0.180 (±0.050) | 1389 |
| No. 9 | EGCG-C18-TE | 0.100 (±0.208) | 320 |

*1 Antiviral effect (50% effective concentration)
*2 Selectivity (Selective Index = $CC_{50}/EC_{50}$)

As can be seen from FIG. 2, by adding each of the EGCG derivatives to the influenza viruses ahead of time, marked reduction in plaque formation was observed as compared with the case where the EGCG was added (open diamond). Furthermore, as can be seen from Table 4, by adding each of the EGCG derivatives to the influenza viruses previously, the antiviral effect stronger than that of EGCG in the comparative example was obtained. In particular, each of EGCG-C12, EGCG-C16, EGCG-C18, EGCG-C18-DE, EGCG-C18-TE had an $EC_{50}$ in the range from 0.02 to 0.118 and thus exhibited an antiviral effect much stronger than that of the EGCG, which had an $EC_{50}$ of 0.391. Among them, EGCG-C18 had a very high SI, which indicates the ratio between the antiviral effect and the toxicity. This demonstrates that EGCG-C18 exhibits an excellent antiviral effect at a low concentration and also has very low toxicity. From this result, it can be said that the EGCG derivatives can inhibit the infectivity of viruses to cells. It also can be said that the EGCG derivatives exhibit an effect of inactivating viruses directly. Moreover, from the fact that the EGCG derivatives were added to the viruses ahead of time, it was found that the membrane fusion inhibitor of the present invention can be used as an agent for preventing viral infection.

Example 2

Whether the EGCG derivative of the present invention targets membrane fusion by HA instead of NA was checked through hemagglutination.

Hemagglutination Assay

EGCG-C16 (EGCG-Pal) prepared in Example 1 was dissolved in D-PBS (0.2% DMSO) so as to prepare sample solutions containing EGCG-C16 at predetermined concentrations. The concentrations of EGCG-C16 in sample solutions were set so that the final concentrations when conducting a treatment to be described later would be 0, 0.25, 0.5, 1, 2, 4, 8, and 16 µmol/l, respectively. 25 µl of each of the sample solutions was applied to a 96-well plate. Further, 25 µl of a suspension of influenza viruses (A/PR8/34/H1N1) obtained by suspending the influenza viruses with D-PBS ($6.5 \times 10^5$ $TCID_{50}$) was applied to the plate. The plate was incubated at room temperature for 30 minutes, and thereafter, 50 µl of an agglutination solution of chicken erythrocytes diluted 200-fold with D-PBS was applied to the plate. The plate was incubated at 4° C. for 1 hour. Thereafter, the degree of agglutination of the erythrocytes was observed, and the agglutination-inhibiting effect of EGCG-C16 was evaluated. As a control, the evaluation was made in the same manner using D-PBS instead of the influenza virus suspension. Furthermore, as a comparative example, EGCG was used instead of EGCG-C16.

Figure 3:
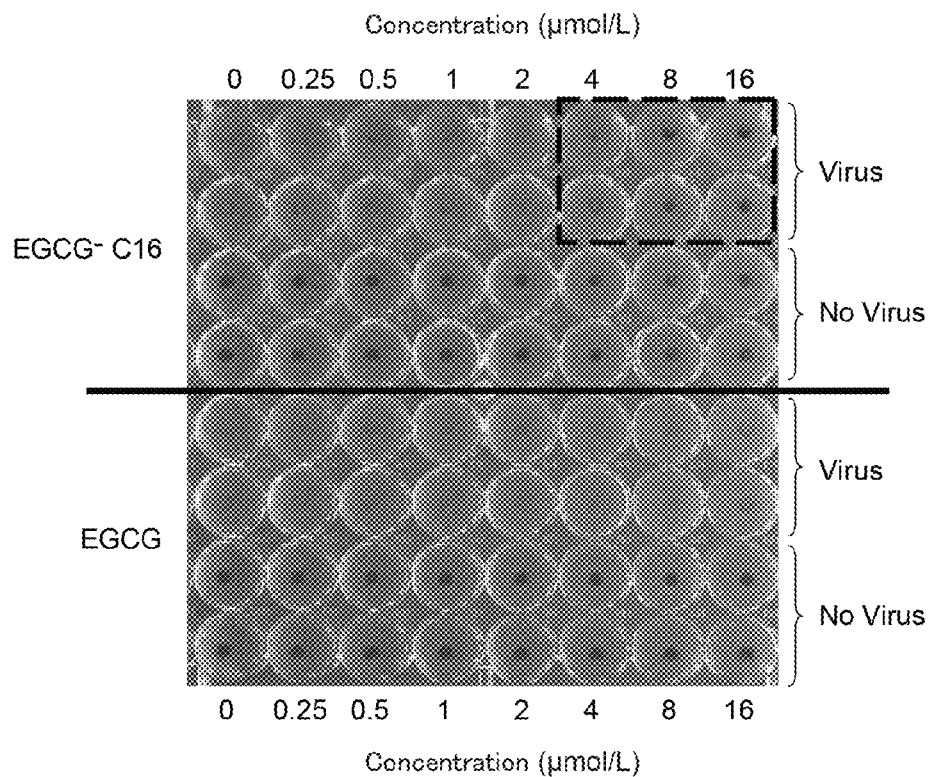
FIG. 3 is a photograph showing the result of a hemagglutination assay performed in the presence of an EGCG derivative in Example 2 of the present invention.

The result thereof is shown in FIG. 3. FIG. 3 is a photograph showing the agglutination of the erythrocytes in the presence of EGCG. In FIG. 3, from the top, the first and second rows indicate the results obtained when EGCG-C16 was used (Virus), the third and fourth rows indicate the results obtained when the control against EGCG-C16 was used (No Virus), and the fifth and sixth rows indicate the results obtained when the EGCG was used (Virus), and the seventh and eighth rows indicate the results obtained when the control against the EGCG was used (No Virus). Moreover, the horizontal lane indicates the result obtained when the concentration (µmol/l) of the EGCG derivatives was changed.

As can be seen from FIG. 3, although agglutination of the erythrocytes was observed when EGCG-C16 was not added (0 µmol/l) in the presence of the viruses, the agglutination of the erythrocytes was suppressed as the concentration of EGCG-C16 increased (4, 8, and 16 µmol/l). From these results, it was found that EGCG-C16 inhibits the membrane fusion by HA. In contrast, in the comparative example, even if the final concentration of the EGCG was increased up to 16 µmol/l, suppression of the agglutination of the erythrocytes was not observed. With regard to the other EGCG derivatives, similar results were obtained. From these results, it can be said that, as in the case of the above-described example, the EGCG derivatives can inhibit viral infection by inhibiting the membrane fusion efficiently.

Example 3

The effect of preventing viral infection to cells and the viral infectivity-inhibiting effect of the EGCG derivatives were compared with those of zanamivir (registered trademark "Relenza") and oseltamivir phosphate (registered trademark "Tamiflu"), which exhibit an antiviral action by the mechanism different from those of the EGCG derivatives.

The viral infection-preventing effect and the inhibition of infectivity were evaluated in the same manner as in Example 1. As a comparative example, the same treatment was carried out except that zanamivir, oseltamivir phosphate, or EGCG was used instead of the EGCG derivatives.

Figure 4:
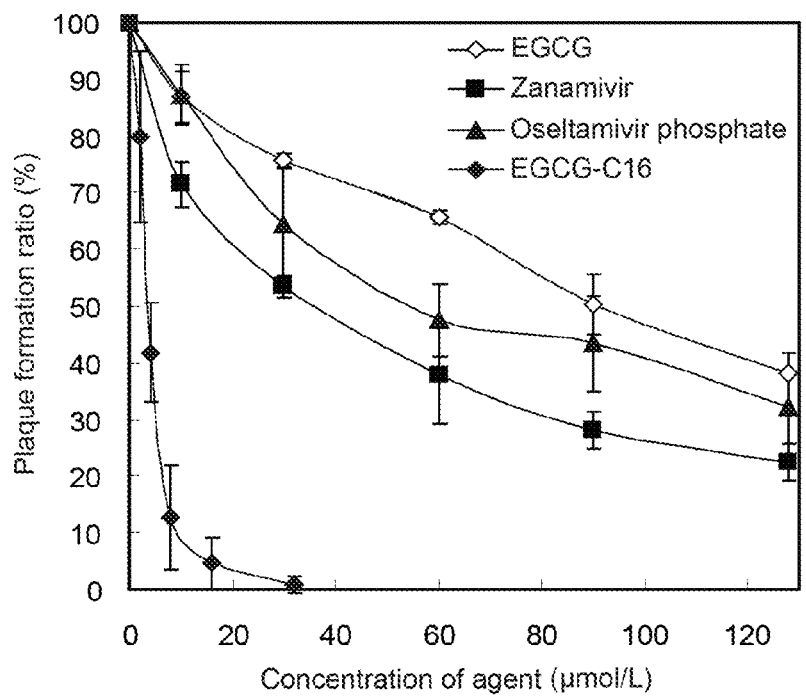
FIG. 4 is a graph showing the relationship between the concentration of an EGCG derivative and the plaque formation in Example 3 of the present invention.

The results obtained regarding the viral infection-preventing effect are shown in FIG. 4 and Table 5 below. FIG. 4 is a graph showing the relationship between the concentration of EGCG-C16 and the plaque formation ratio. As can be seen from FIG. 4, by adding EGCG-C16 to the cells ahead of time, the plaque formation could be reduced much more effectively than in the comparative example. With regard to the other EGCG derivatives, similar effects were obtained. Furthermore, as can be seen from Table 5 below, by adding the EGCG derivatives to the cells previously, the viral infection-preventing effect much stronger than that in the comparative example was exhibited. Specifically, the EGCG derivatives exhibited the viral infection-preventing effect that was about 5.4 to 12.7 times stronger than that of zanamivir, about 8.3 to 19.3 times stronger than that of oseltamivir phosphate, and about 13.5 to 31.6 times stronger than that of the EGCG.

TABLE 5

| Viral infection-preventing effect | | |
|---|---|---|
| | Antiviral agent or Membrane fusion inhibitor | $EC_{50}$*[1] (µmol/l) |
| Comparative example | zanamivir | 38.01 |
| | oseltamivir phosphate | 58.22 |
| | EGCG | 94.65 |
| Example | EGCG-C15-Far | 4.0 |
| | EGCG-C16 | 4.02 |
| | C18-DE | 7.0 |
| | C18-TE | 3.0 |

*[1]Antiviral effect (50% effective concentration)

Figure 5:
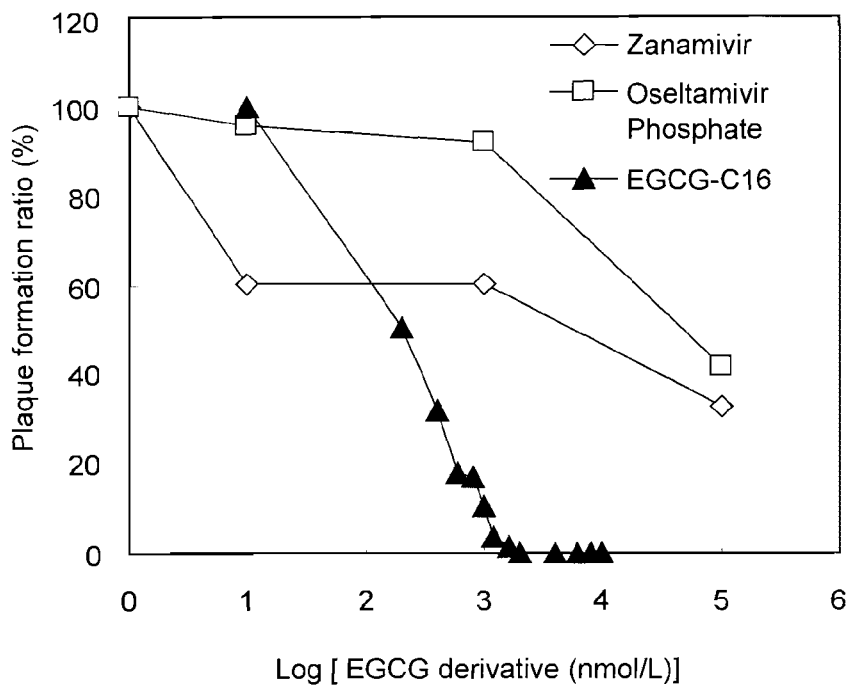
FIG. 5 is a graph showing the relationship between the concentration of an EGCG derivative and the plaque formation in Example 3 of the present invention.

Next, the results obtained regarding the inhibition of viral infectivity are shown in FIG. 5 and Table 6 below. FIG. 5 is a graph showing the relationship between the concentration of EGCG-C16 and the plaque formation ratio. As can be seen from FIG. 5, by adding EGCG-C16 to the viruses ahead of time, the plaque formation can be reduced more effectively than in the comparative example. With regard to the other EGCG derivatives, similar results were obtained. Furthermore, as can be seen from Table 6 below, by adding the EGCG derivatives to the viruses previously, the viral infectivity could be inhibited more strongly than in the comparative example. Specifically, the EGCG derivatives exhibited the viral infectivity-inhibiting effect that was about 21 to 315 times stronger than that of zanamivir, about 187 to 2810 times stronger than that of oseltamivir phosphate, and about 1.3 to 20 times stronger than that of the EGCG.

TABLE 6

Viral infectivity-inhibiting effect

| | Antiviral agent or Membrane fusion inhibitor | $EC_{50}$*1 ($\mu$mol/l) |
|---|---|---|
| Comparative example | zanamivir | 6.3 |
| | oseltamivir phosphate | 56.2 |
| | EGCG | 0.391 |
| Example | EGCG-C16 | 0.020 |
| | EGCG-C18 | 0.060 |
| | C18-DE | 0.180 |
| | C18-TE | 0.200 |

*1 Antiviral effect (50% effective concentration)

These results demonstrate that the EGCG derivatives can inhibit viral infection more efficiently than EGCG and conventional antiviral agents.

Example 4

The therapeutic effect of EGCG-C16 on cells infected with viruses was examined.

Figure 6:
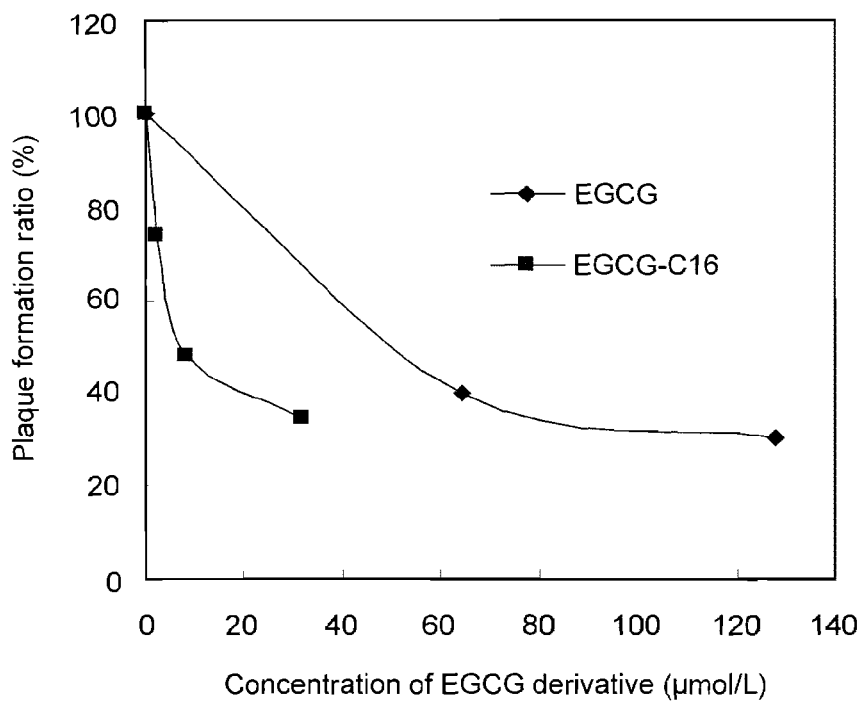
FIG. 6 is a graph showing the relationship between the concentration of an EGCG derivative and the plaque formation in Example 4 of the present invention.

EGCG-C16 was dissolved in Opti-MEM (0.2% DMSO) so as to prepare sample solutions containing EGCG-C16 at predetermined concentrations (0, 2, 8, 32, 64, and 128 nmol/l). Canine kidney cultured cells (MDCK) were cultured on a 6-well plate until confluent. The culture solution was removed from the plate, and the cultured cell sheets were washed with D-PBS. Thereafter, 700 µl of influenza viruse (A/PR8/34/H1N1) solution suspend with DMEM (0.2% BSA) was applied to the cell sheets at an MOI of $2.5 \times 10^{-4}$. The cell sheets were incubated at room temperature for 1 hour, after which the cell sheets were washed with D-PBS. 700 µl of each of the EGCG-C16 sample solutions was applied to the cell sheet, and the cell sheet then was incubated at 37° C. for 2 hours in the presence of $CO_2$. The sample solution was removed, and the cell sheet was washed with D-PBS. Thereafter, 0.8% agarose gel containing $6.0 \times 10^{-4}$% trypsin and 0.2% BSA was layered on the cell sheet. The cell sheet further was incubated at 37° C. for 52 to 60 hours in the presence of $CO_2$, and thereafter, the number of plaques appearing on each cell sheet was counted. Then, assuming that the number of plaques on the cell sheet to which no EGCG derivative had been added (0 µmol/l) was 100, the plaque formation ratio (%) was calculated, thus evaluating the viral infection-preventing effect of the EGCG derivative. As a comparative example, the same treatment was carried out using EGCG to which no acyl group was introduced, instead of the EGCG derivative. The result thereof is shown in FIG. 6. FIG. 6 is a graph showing the relationship between the concentration of the EGCG derivative and the plaque formation ratio.

As can be seen from FIG. 6, by adding the EGCG derivative to the cells infected with the viruses, plaque formation was reduced markedly as compared with the case where the EGCG was added. With regard to the other EGCG derivatives, similar results were obtained. From this result, it was found that, even when the cells that already have been infected with viruses are present, it is possible to suppress the release of the viruses from the infected cells. It can be said that this can inhibit further infection with the viruses released from the infected cells.

Example 5

The infection-preventing effect of EGCG derivatives in vivo was examined.

Mice (Bulb/C, female, 6-week old) were divided into four groups, Groups A to D, each consisting of five mice, and they were caged separately on a group-by group basis. The mice of the respective groups were subjected to the following treatments with different conditions.

Group A: administration of EGCG-C16(−)/influenza virus infection(−)

Group B: administration of EGCG-C16(+)/influenza virus infection(−)

Group C: administration of EGCG-C16(−)/influenza virus infection(+)

Group D: administration of EGCG-C16(+)/influenza virus infection(+)

Figure 7:
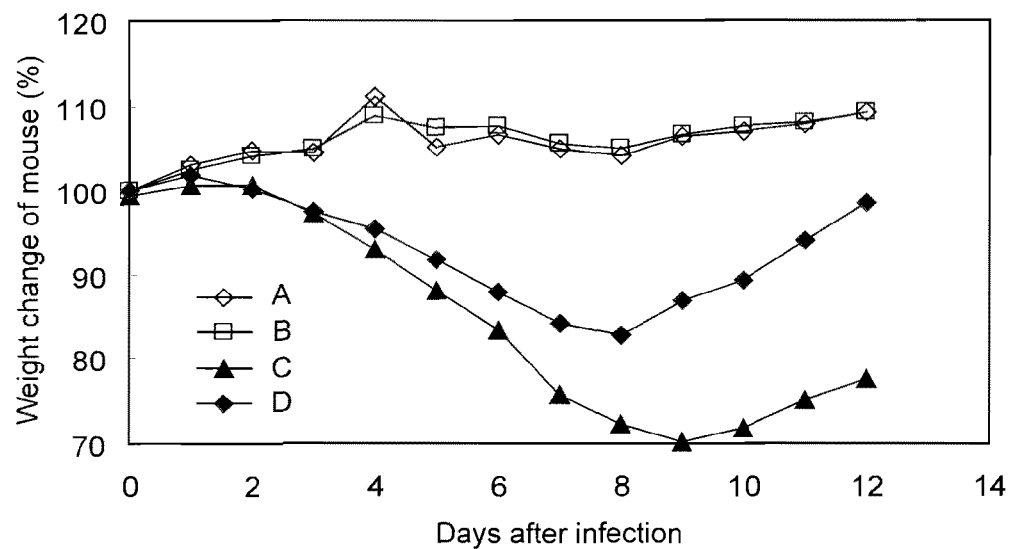
FIG. 7 is a graph showing the change with time in weight of mice after viral infection in Example 5 of the present invention.

Each of the mice was etherized. D-PBS (2% DMSO) was inoculated intranasally into the mice of Groups A and C, and 20 µl of D-PBS (2% DMSO) solution containing 718 µmol/l EGCG-C16 was inoculated intranasally into the mice of Groups B and D. Two hours later, to the mice anesthetized with a 10% Nembutal solution injected intraperitoneally, 20 µl of $5 \times 10^6$ TCID50/ml influenza viruses (A/FM1/H1N1) were inoculated intranasally. After the intranasal inoculation of the viruses, the weight of each mouse was measured every other day, and the change in weight and the survival rate were evaluated. The result thereof is shown in FIG. 7. FIG. 7 is a graph showing the change with time in weight of the mice after viral infection.

In the mice of Groups A and B as controls not infected with the influenza viruses, no change in weight was observed. In the mice of Group C to which the EGCG derivative was not administered, their weight decreased drastically owing to the infection with the influenza viruses. In contrast, in the mice of Group D to which the EGCG derivative was administered previously, although their weights decreased slightly for about one week, they increased abruptly thereafter. Thus, by administering the EGCG derivative previously, weight loss due to the viral infection can be suppressed. Therefore, it can be said that, according to the EGCG derivative of the present invention, it is possible to prevent the pathological condition after being infected with influenza viruses from becoming severe.

Example 6

With regard to an EGCG derivative having an acyl group in the D ring and an EGCG derivative having an acyl group in the B ring, the antiviral effect was examined.

EGCG-C16 was prepared in the same manner as in Example 1. As EGCG-C16, a mixture of a derivative represented by the chemical formula (2) in which the 3-position ($R^1$) in the B ring is a palmitoyl group (C16) and a derivative represented by the chemical formula (2) in which the 4-position ($R^2$) in the B ring is a palmitoyl group (hereinafter, the mixture is referred to as a "B-ring derivative"), and a mixture of a derivative represented by the chemical formula (2) in which the 4-position ($R^5$) in the D ring is a palmitoyl group (C16) and a derivative represented by the chemical formula (2) in which the 6-position ($R^6$) in the D ring is a palmitoyl group (hereinafter, the mixture is referred to as a "D-ring derivative") were used. Note here that, in the chemical formula (2), Rs other than the above-described Rs are all hydrogen atoms.

1.25 µl of 10 mg/ml mouse microsome (Charles River Laboratories Japan, Inc.) and 0.25 µl of an aqueous solution of 1% 3-[(3-cholamidopropyl)dimethyl ammonio]-1-propanesulfonate (CHAPS, Dojindo) were dissolved in 8.5 µl of an aqueous solution of 0.1 mol/l potassium phosphate (pH 7.4). The resultant solution was incubated on ice for 30 minutes so as to elute a glucuronic acid metabolic enzyme in the microsome. This solution was used as a reaction solution A. Next, 10 µl of 10 mmol/l EGCG-C16, 5.0 µl of 10 mg/ml L-α-lysophosphatidylcholine (Wako) and 20 µl of 30 mmol/l UDP-glucuronic acid trisodium (UDP-Glc; Nacalai Tesque, Inc.) were dissolved in 155 µl of reaction buffers (1.0 mol/l Tris-HCl (pH 7.4): 0.1 mol/l $MgCl_2$: $H_2O$=2:1:13), respectively. The resultant mixtures were used as reaction solutions B, respectively. Subsequently, in a hot-water bath at 37° C., the reaction solution A and each of the reaction solutions B were mixed, thereby causing a reaction for conjugating glucuronic acid of EGCG-C16. After allowing each mixture to react for predetermined times (0, 0.5, 1, 1.5, 3, 6, 12, 24 minutes), 200 µl of acetonitrile (HPLC grade; KANTO CHEMICAL CO., INC.) was added per 200 µl of the reaction solution to terminate the metabolic reaction. Subsequently, the reaction solution was filtered through a 0.45 µm DISMIC (registered trademark) filter made of PTFE (Ekicrodisc 13CR; Gelman Science), after which about 40 µl of the reaction solution was subjected to HPLC analysis under the following conditions.

Figure 8:
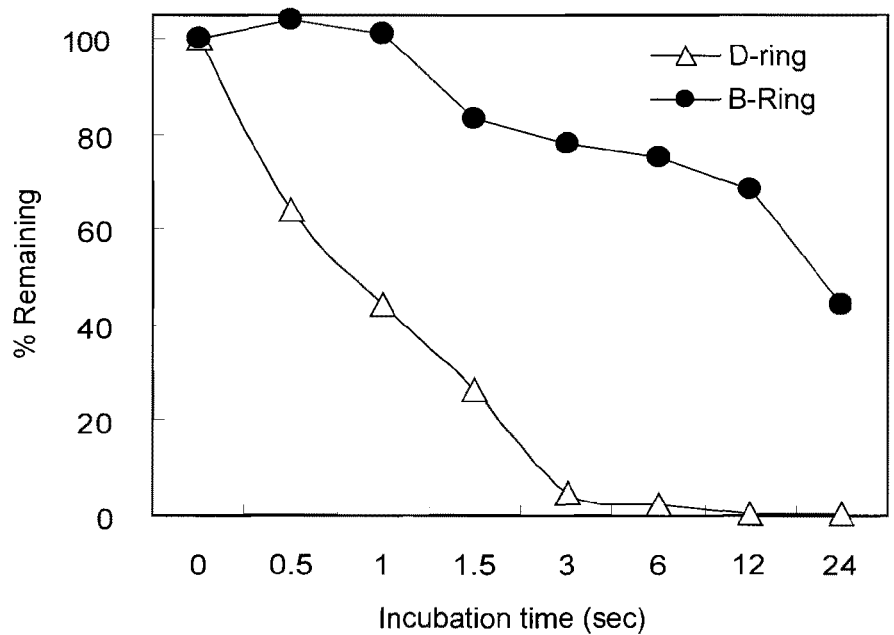
FIG. 8 is a graph showing the remaining ratio of EGCG derivatives in the presence of a glucuronic acid metabolic enzyme derived from mouse microsome in Example 6 of the present invention.

A WP300-C4 column (5 µm, 4.6×150 mm, GL Science) was mounted on a HPLC analysis system (JASCO Corporation), and each of the metabolic reaction solutions of EGCG-C16 was analyzed at a wavelength of 265 nm. For a mobile phase of the HPLC analysis, distilled water (HPLC grade; KANTO CHEMICAL CO., INC.) containing 0.1% trifluoro acetic acid (HPLC grade; Wako) was used as a solution A and acetonitrile (HPLC grade; KANTO CHEMICAL CO., INC.) containing 0.1% trifluoro acetic acid was used as a solution B. The percentage by volume of the solution B in the whole (the solution A+solution B) was set so as to provide gradient, specifically, set to 0%, 0%, 25%, 100%, 100%, 0%, and 0% at an elution time of 0, 3, 10, 22, 26, 28, and 30 minutes, respectively. The analysis was conducted at a flow rate of 1.5 ml/min. Then, assuming that the peak area of EGCG-C16 in the unreacted reaction solution was 100%, the ratio of the peak area of EGCG-C16 in the reaction solution after a lapse of the predetermined time was determined as a remaining ratio (%) of EGCG-C16. As a comparative example, the same treatment was carried out using EGCG to which no acyl group was introduced, instead of the EGCG derivatives. These results are shown in FIG. 8. FIG. 8 is a graph showing the relationship between the reaction time of EGCG-C16 and the remaining ratio of EGCG-C16. In FIG. 8, "D-ring" indicates the D-ring derivative, and the "B-ring" indicates the B-ring derivative.

As can be seen from FIG. 8, after a lapse of 24 minutes, the peak area of the D-ring derivative was reduced to 0.5% of that at the start of the reaction, whereas the remaining ratio of the B-ring derivative was 44%. Thus, it was found that the B-ring derivative exhibits higher metabolic stability than the D-ring derivative.

Example 7

With regard to EGCG-C16 having an acyl group in the D ring and EGCG-C16 having an acyl group in the B ring, the viral infection-preventing effect was examined.

Figure 9:
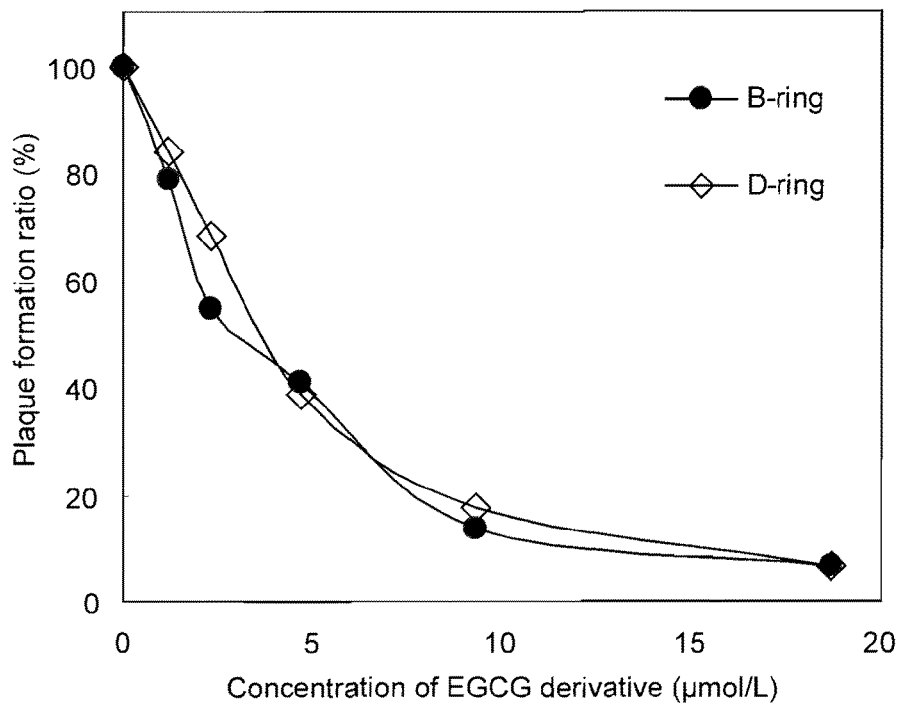
FIG. 9 is a graph showing the relationship between the concentration of EGCG derivative and the plaque formation in Example 7 of the present invention.

The B-ring derivative or the D-ring derivative used in Example 6 was added to cells ahead of time and the viral infection-preventing effect of the EGCG derivatives was examined in the same manner as in Example 1. The result thereof is shown in FIG. 9. FIG. 9 is a graph showing the relationship between the concentration of the B-ring and D-ring derivatives and the plaque formation ratio. As can be seen from FIG. 9, no difference in the antiviral effect was observed between the B-ring derivative and the D-ring derivative, and it was found that both of them similarly exhibit an excellent antiviral effect. Furthermore, the B-ring derivative was divided into a derivative in which the 3-position ($R^1$) is a palmitoyl group (C16) and a derivative in which the 4-position ($R^2$) is a palmitoyl group, and the antiviral effect of these derivatives was examined in the same manner. As a result, no difference in the effect was observed between these isomers, and it was found that both of the isomers similarly exhibit an excellent antiviral effect. Also, the D-ring derivative was divided into a derivative in which the 4-position ($R^5$) is a palmitoyl group (C16) and a derivative in which the 6-position ($R^6$) is a palmitoyl group, and the antiviral effect of these derivatives was examined in the same manner. As a result, no difference in the effect was observed between these isomers, and it was found that both of the isomers similarly exhibit an excellent antiviral effect. With regard to the EGCG derivatives other than EGCG-C16, similar results were obtained.

Example 8

The antiviral effect of EGCG derivatives having an acyl group with the same main chain length was examined.

With regard to EGCG-C18, EGCG-C18-DE, and EGCG-C18-TE prepared in Example 1, the viral infection-preventing effect and the viral infectivity-inhibiting effect were examined. These EGCG derivatives each have an acyl group having a main chain length of 18.

Figure 10:
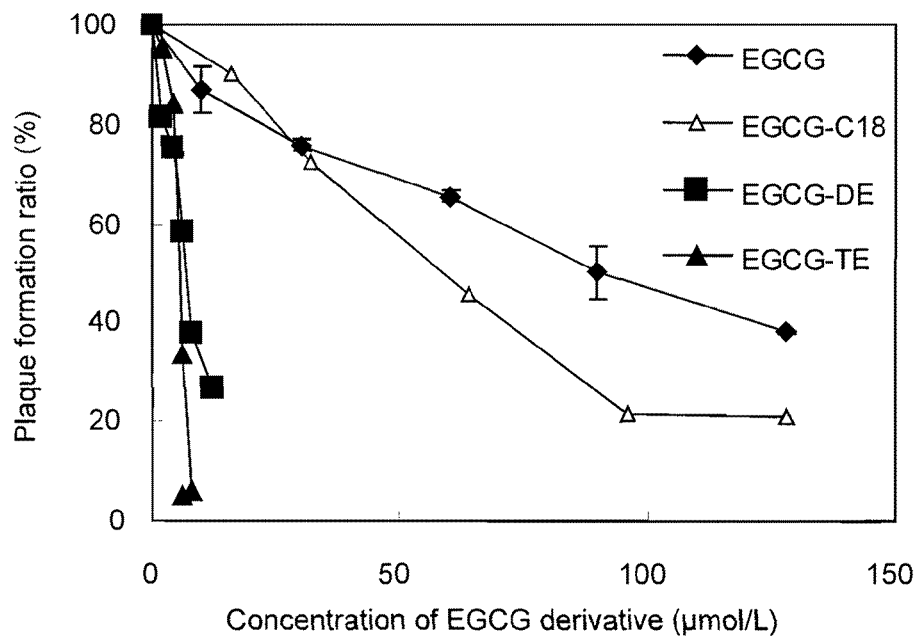
FIG. 10 is a graph showing the relationship between the concentration of EGCG derivatives and the plaque formation in Example 8 of the present invention.

First, each of the EGCG derivatives were added to cells previously and the viral infection-preventing effect of the EGCG derivatives was examined in the same manner as in Example 1. As a comparative example, the viral infection-preventing effect of EGCG was examined in the same manner. The result thereof is shown in FIG. 10. FIG. 10 is a graph showing the relationship between the concentration of each of the EGCG derivatives and the plaque formation ratio. As can be seen from FIG. 10, all the EGCG derivatives could reduce the plaque at a lower concentration as compared with the EGCG. Among them, EGCG-C18-DE (EGCG-DE) and EGCG-C18-TE (EGCG-TE), each having an unsaturated bond in the acyl group, could reduce the plaque formation efficiency at a very low concentration, and in particular, the effect of EGCG-C18-TE was remarkable. From these results, it was found that, among EGCG derivatives having an acyl group with the same main chain length, the one with an unsaturated bond exhibits a stronger viral infection-preventing effect, and as the number of unsaturated bonds increases, the viral infection-preventing effect becomes stronger.

Figure 11:
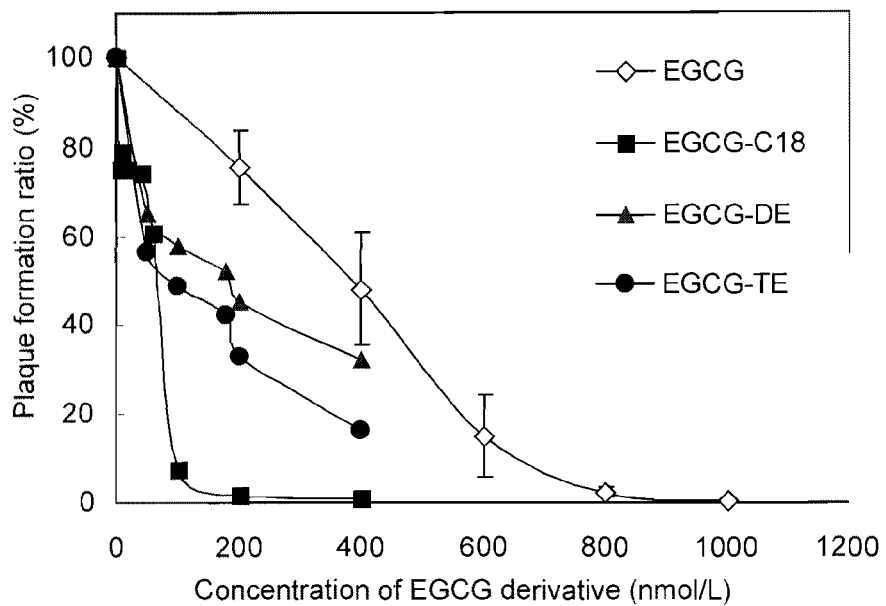
FIG. 11 is a graph showing the relationship between the concentration of EGCG derivatives and the plaque formation in Example 8 of the present invention.

Also, each of the EGCG derivatives was added to viruses ahead of time and the viral infectivity-inhibiting effect was examined in the same manner as in Example 1. As a comparative example, the infectivity-inhibiting effect of EGCG was examined in the same manner. The result thereof is shown in FIG. 11. FIG. 11 is a graph showing the relationship between the concentration of each EGCG derivative and the plaque formation ratio. As can be seen from FIG. 11, all the EGCG derivatives could reduce the plaque at a lower concentration as compared with the EGCG. Among them, EGCG-C18 in which the acyl group is a saturated fatty acid could reduce the plaque formation efficiently at a very low concentration. These results demonstrate that, among EGCG derivatives having an acyl group with the same main chain length, the one in which the acyl group is a saturated fatty acid exhibits a stronger infectivity-inhibiting effect.

Example 9

The viral infection-inhibiting effect by an EGCG derivative in embryonated hen eggs was examined.

A 0.2% DMSO-containing Opti-MEM solution containing EGCG-C16 and influenza A viruses (A/H5N1) was prepared. The solution was prepared so that 1.25 μmol/l of EGCG-C16 and 100 TCID50/egg of the influenza viruses were present therein. This mixed solution of catechin and the viruses were incubated at 20° C. for 30 minutes, and then, 100 μl of the mixed solution was inoculated into 12-day-old embryonated hen eggs (n=8). Then, the embryonated hen eggs were incubated at 37° C. for 30 minutes. Thereafter, the survival rate (%) of the embryonated hen eggs over time was examined. Furthermore, as a comparative example, Tamiflu or EGCG was inoculated instead of the EGCG derivative, and the survival rate was examined in the same manner. Also, as a control, the survival rate of embryonated hen eggs to which only influenza viruses were inoculated without inoculating the EGCG derivatives was examined in the same manner.

Figure 12:
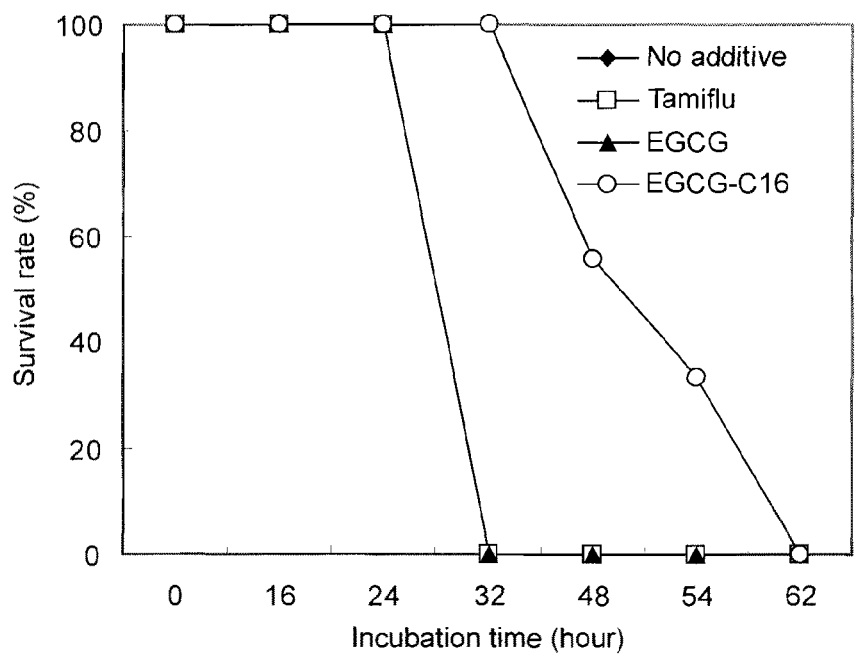
FIG. 12 is a graph showing the survival rate of embryonated hen eggs in the presence of an EGCG derivative in Example 9 of the present invention.

The result thereof is shown in FIG. 12. FIG. 12 is a graph showing the survival rate of the embryonated hen eggs over time. In FIG. 12, the survival rate is a relative value (%) obtained assuming that the survival rate when all of the eight embryonated hen eggs were alive is 100%. As can be seen from FIG. 12, in the cases where no EGCG derivative was added (filled diamond), EGCG was added (filled triangle), and Tamiflu was added (open square), the same behavior was exhibited and all the embryonated hen eggs died in 32 hours of the incubation. In contrast, it was found that EGCG-C16 (open circle) allows the embryonated hen eggs to stay alive for a long time.

Furthermore, using D-PBS (2% DMSO) solutions respectively containing EGCG-C16 at predetermined concentrations (0.5, 1, 5, and 10 μmol/l), the survival rate was examined (n=8) in the same manner as described above 24 hours after the inoculation of the influenza viruses, except that the inoculation condition of the influenza viruses to the embryonated hen eggs was set to 0.1, 1.0, or 10TCID50/egg.

Figure 13:
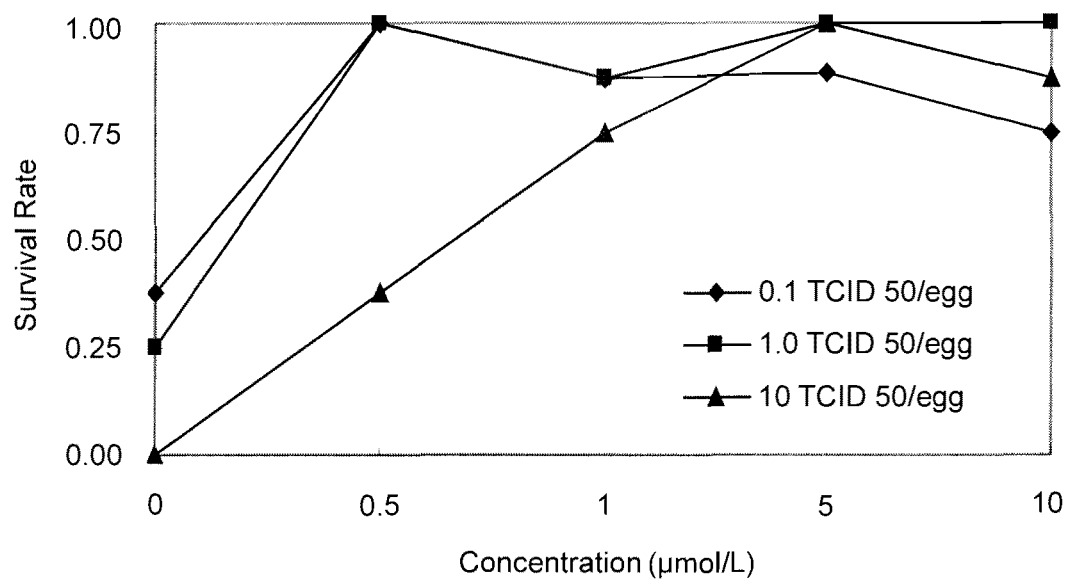
FIG. 13 is a graph showing the survival rate of embryonated hen eggs in the presence of an EGCG derivative in Example 9 of the present invention.

The result thereof is shown in FIG. 13. FIG. 13 is a graph showing the survival rate of the embryonated hen eggs when using the EGCG derivative at the respective concentrations. In FIG. 13, the survival rate is a relative value obtained assuming that the survival rate when all of the eight embryonated hen eggs were alive is 1. As can be seen from FIG. 13, even when the concentration of the inoculated influenza viruses was increased, the survival rate sufficiently could be prevented from decreasing by increasing the concentration of the EGCG derivative.

Example 10

The infectivity-inhibiting effect of EGCG derivatives against various kinds of viruses was examined.

As viruses, A/Beijing/262/95 (H1N1), A/Panama/2007/99 (H3N2), and Influenza B/Yamanashi/166/98 were used, and as an EGCG derivative, EGCG-C16 was used. The infectivity-inhibiting effect of the EGCG derivative was examined in the same manner as in Example 1, except that the EGCG derivative was added to the respective types of viruses previously. As a comparative example, the infectivity-inhibiting effect of EGCG was examined in the same manner.

Figure 14A:
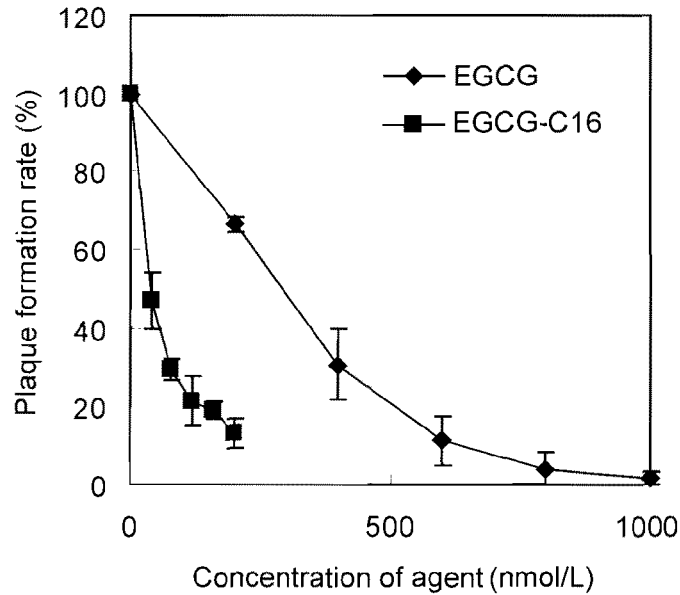
FIGS. 14A to 14C are graphs each showing the relationship between the concentration of an EGCG derivative and the plaque formation in Example 10 of the present invention.
Figure 14B:
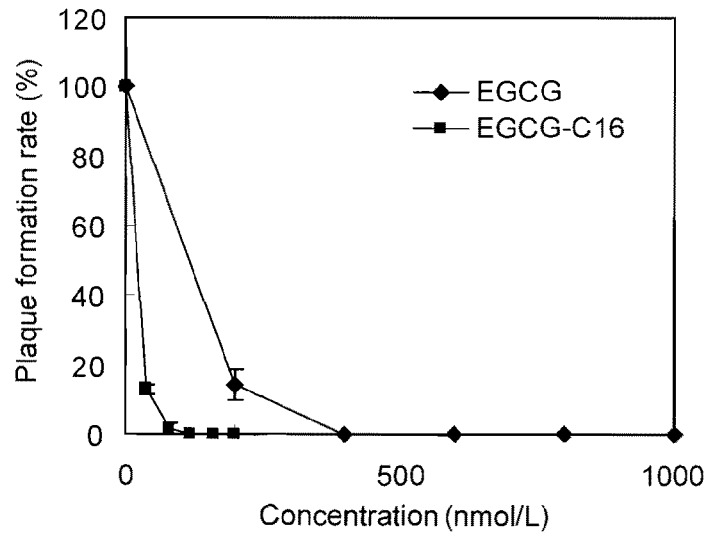
Figure 14C:
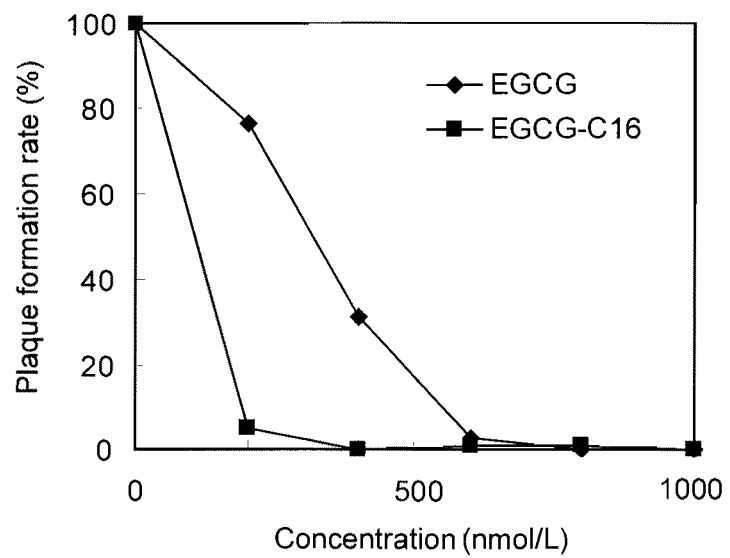

The result thereof is shown in FIGS. 14A to 14C. FIG. 14A is a graph showing the plaque formation ratio regarding A/Beijing/262/95 (H1N1), FIG. 14B is a graph showing the plaque formation ratio regarding A/Panama/2007/99 (H3N2), and FIG. 14C is a graph showing the plaque formation ratio regarding InfluenzaB/Yamanashi/166/98. As can be seen from FIGS. 14A to 14C, as compared with EGCG, EGCG-C16 markedly reduced the plaque formation by all the types of viruses. Thus, it was found that the EGCG derivative according to the present invention exhibits excellent effect against various types of viruses.

Example 11

Cells were infected with viruses to which EGCG derivatives were added ahead of time, and the presence or absence of the expression of virus proteins, namely, hemagglutinin (HA) and a matrix protein (MI), was examined.

EGCG-C16 was dissolved in Opti-MEM (0.2% DMSO) so as to achieve a predetermined concentration (20 nmol/l). Influenza viruses (A/PR8/34/H1N1) further were added thereto. Thus, a sample solution was prepared. This sample solution was incubated at room temperature for 30 minutes. On the other hand, on a 6-well plate filled with a culture solution, canine kidney cultured cells (MDCK) were cultured until confluent (about 8 hours). The culture solution was removed from the plate, and the cultured cell sheets were washed with D-PBS. Thereafter, the sample solution having undergone the incubation was applied to the cell sheets so that the MOI of the influenza viruses would be 0.15. The cell sheets were incubated at room temperature for 1 hour, and 0.8% agarose gel containing $6.0 \times 10^{-4}$% trypsin and 0.2% BSA was layered on each of the cell sheets. The cell sheets further were incubated at 37° C. for predetermined times (6, 8, and 10 hours) in the presence of $CO_2$. The cells having cultured for the predetermined times were immobilized using methanol, and HA and MI were detected using primary antibodies and secondary antibodies. As the primary antibodies, anti-HA antibodies (product name "Mouse Anti-influenza A hemagglutinine", available from Abcam, dilution ratio: 1:1000, diluent: 2% milk in PBS-tween) or anti-MI antibodies (product name "Mouse Anti-influenza A matrix", available from AbD, dilution ratio: 1:1000, diluent: 2% milk in PBS-tween) were used. As the secondary antibodies, Texas Red-labeled antibodies (product name "Anti-IgG Mouse-Goat Texas Red", Funakoshi Co., Ltd., dilution ratio: 1:1000, diluent: 2% milk in PBS-tween) were used. Furthermore, as a negative control, instead of the sample solution containing EGCG-C16, Opti-MEM (0.2% DMSO) containing no EGCG derivative was added to the cultured cells, and HA and MI were detected in the same manner.

Figure 15:
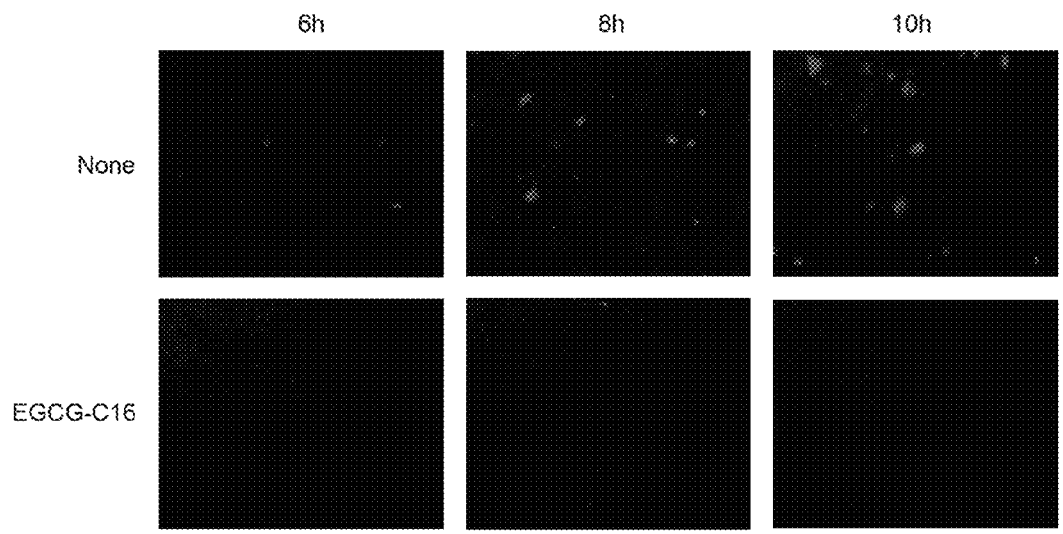
FIG. 15 shows photographs showing the presence or absence of HA protein expression in the presence of an EGCG derivative in Example 11 of the present invention.
Figure 16:
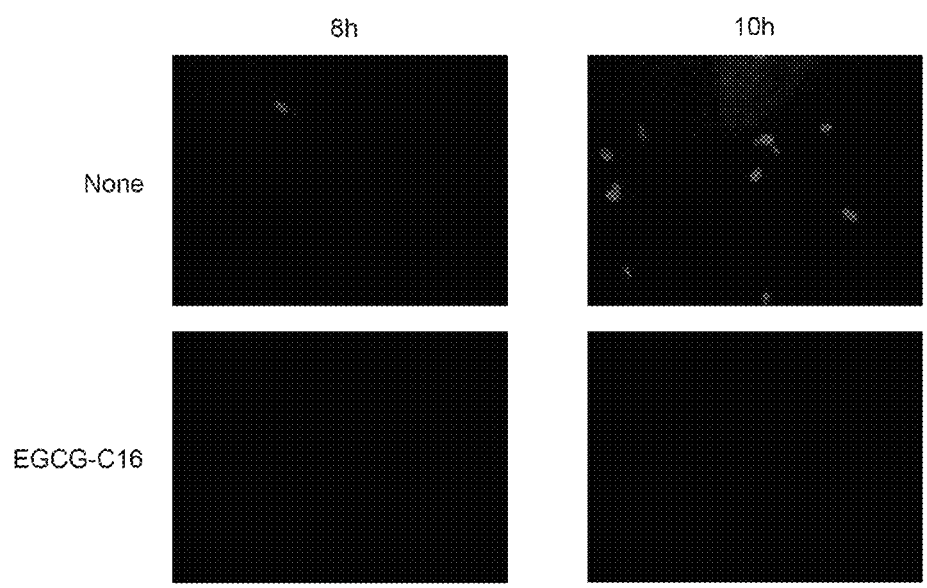
FIG. 16 shows photographs showing the presence or absence of M1 protein expression in the presence of an EGCG derivative in Example 11 of the present invention.

The result thereof is shown in FIGS. 15 and 16. FIG. 15 shows photographs showing the expression of HA in the cultured cells, and FIG. 16 shows photographs showing the expression of MI in the cultured cells. In FIGS. 15 and 16, the upper row indicates the results obtained regarding the negative control, the lower row indicates the results obtained when EGCG-C16 was added, and "h" indicates the incubation time. As can be seen from the upper rows of FIGS. 15 and 16, in the case where no EGCG derivative was added, the expressions of HA and MI were observed after the culture of 8 hours or longer. In contrast, as can be seen from the lower rows of FIGS. 15 and 16, by adding the EGCG derivative to the viruses ahead of time, HA and MI were not observed even after the culture of 10 hours or longer. These results demonstrate that expressions of HA and MI derived from the viruses in the cells were suppressed by the EGCG derivative. Thus, according the EGCG derivative, it becomes possible to inhibit a stage before the virus proteins propagate in the infected cells. Also, since the EGCG derivative can inhibit the stage before the virus proteins increase in the infected cells, it is apparent that, by using the EGCG derivative in combination with, for example, a conventional M2 inhibitor and an NA inhibitor such as zanamivir (registered trademark "Relenza") or oseltamivir (oseltamivir phosphate; registered trademark "Tamiflu"), two-stage blocking becomes possible. Moreover, it is also apparent that the EGCG derivative is effective against viruses resistant to M2 inhibitors and NA inhibitors.

INDUSTRIAL APPLICABILITY

According to the present invention, in an infection step in the virus propagation cycle, it is possible to inhibit the membrane fusion between the membrane of the phagosome enclosing the virus (derived from the cell) and the envelope of the virus (the membrane of the virus). Since the membrane fusion itself is inhibited as described above, steps downstream therefrom, i.e., the uncoating and the replication themselves can be blocked. Furthermore, since the membrane fusion inhibitor of the present invention targets a different step than conventional antiviral agents, it also can inhibit viral infection that cannot be blocked by conventional M2 inhibitors and NA inhibitors, for example. Still further, in the present invention, EGCG as the basic skeleton is, for example, catechin contained in tea and the like, and it is well known that catechin is excellent in safety. Also, the acyl group(s) of $R^1$ to $R^6$ is excellent in safety. Therefore, it also can be said that the membrane fusion inhibitor of the present invention is a pharmaceutical composition that also has excellent safety.

The invention claimed is:

1. A membrane fusion inhibitor that inhibits viral membrane fusion, the membrane fusion inhibitor comprising:
    first, second, third and fourth epigallocatechin gallate derivatives, wherein each of the first, second, third and fourth derivatives is represented by the following general chemical formula (1), an isomer thereof, or a salt thereof, $$(1)$$

where:
    each of $R^1$ to $R^6$ is a hydrogen atom, sodium, potassium, or an acyl group and may be identical to or different from one another,
    the acyl group is a linoleyl group or a linolenyl group, and may be substituted with one or more substituents selected from the group consisting of an alkyl group, an amino group, an alkylamino group, and a dialkylamino group,
    each of $R^7$ to $R^{11}$, $R^{13}$, $R^{15}$, and $R^{16}$ is a hydrogen atom, and each of $R^{12}$ and $R^{14}$ is a hydrogen atom, sodium, or potassium and may be identical to or different form one another,
    wherein in the first epigallocatechin gallate derivative, $R^1$ is the acyl group;
    wherein in the second epigallocatechin gallate derivative, $R^2$ is the acyl group;
    wherein in the third epigallocatechin gallate derivative, $R^5$ is the acyl group;
    wherein in the fourth epigallocatechin gallate derivative, $R^6$ is the acyl group,
    wherein the first, second, third and fourth epigallocatechin gallate derivatives are different from one another, and
    wherein at least one of the first, second, third and fourth epigallocatechin gallate derivatives is a monoacylated epigallocatechin gallate derivative.

2. The membrane fusion inhibitor according to claim 1, wherein in $R^1$ to $R^6$ in the general chemical formula (1),
    (i) the alkyl group is a straight-chain or branched alkyl group having 1 to 6 carbon atoms,
    (ii) an alkyl group in the alkylamino group is a straight-chain or branched alkyl group having 1 to 6 carbon atoms, and
    (iii) an alkyl group in the dialkylamino group is a straight-chain or branched alkyl group having 1 to 6 carbon atoms,
    wherein the alkyl groups in (i)-(iii) may be identical to or different from one another.

3. The membrane fusion inhibitor according to claim 1, wherein in $R^1$ to $R^6$ in the general chemical formula (I),
    the alkyl group is a methyl group,
    the alkylamino group is a methylamino group, and
    the dialkylamino group is a dimethylamino group.

4. The membrane fusion inhibitor according to claim 1, wherein in $R^1$ to $R^6$ in the general chemical formula (1), at least one of $R^1$, $R^2$, $R^5$, and $R^6$ is the acyl group, and the rest are each a hydrogen atom.

5. The membrane fusion inhibitor according to claim 1, wherein $R^7$ to $R^{16}$ are each a hydrogen atom.

6. The membrane fusion inhibitor according to claim 1, wherein the membrane fusion inhibitor is effective against at least one virus selected from the group consisting of viruses lacking neuraminidase, viruses resistant to neuraminidase inhibitors, viruses lacking M2, and viruses resistant to M2 inhibitors, wherein the virus is an influenza virus.

7. An expression inhibitor that inhibits expression of a protein of a virus, the expression inhibitor comprising the membrane fusion inhibitor according to claim 1.

8. The expression inhibitor according to claim 7, wherein the protein is at least one of a hemagglutinin protein and a matrix protein.

9. An antiviral agent comprising the membrane fusion inhibitor according to claim 1.

10. The antiviral agent according to claim 9, further comprising at least one of a neuraminidase inhibitor and an M2 inhibitor.

11. The antiviral agent according to claim 9, wherein the antiviral agent is effective against at least one virus selected from the group consisting of viruses lacking neuraminidase, viruses resistant to neuraminidase inhibitors, viruses lacking M2, and viruses resistant to M2 inhibitors, wherein the virus is an influenza virus.

12. A method for inhibiting viral infection, comprising:
administering the membrane fusion inhibitor according to claim 1 to a subject, wherein the viral infection is an influenza viral infection.

* * * * *